US010169662B2

(12) United States Patent
Silberschatz et al.

(10) Patent No.: US 10,169,662 B2
(45) Date of Patent: Jan. 1, 2019

(54) REMOTE BIOMETRIC MONITORING SYSTEM

(71) Applicant: Google LLC, Mountain View, CA (US)

(72) Inventors: Paul Joseph Silberschatz, San Francisco, CA (US); David Carl Janssens, San Francisco, CA (US); Evan David Shapiro, San Francisco, CA (US); Adam Daniel Carlucci, San Francisco, CA (US)

(73) Assignee: Google LLC, Mountain View, CA (US)

( * ) Notice: Subject to any disclaimer, the term of this patent is extended or adjusted under 35 U.S.C. 154(b) by 0 days.

(21) Appl. No.: 15/182,515

(22) Filed: Jun. 14, 2016

(65) Prior Publication Data

US 2016/0364617 A1 Dec. 15, 2016

Related U.S. Application Data

(60) Provisional application No. 62/175,613, filed on Jun. 15, 2015.

(51) Int. Cl.
*G06K 9/00* (2006.01)
*A61B 5/11* (2006.01)
(Continued)

(52) U.S. Cl.
CPC ........ *G06K 9/00771* (2013.01); *A61B 5/0205* (2013.01); *A61B 5/1103* (2013.01);
(Continued)

(58) Field of Classification Search
CPC ...... A61B 5/0002; G06F 19/345; G08B 25/10
(Continued)

(56) References Cited

U.S. PATENT DOCUMENTS 4,289,326 A * 9/1981 Hawkes ................. B62B 1/047
248/171
6,826,315 B1 * 11/2004 Wickes .............. H04N 1/32122
348/207.1
(Continued)

FOREIGN PATENT DOCUMENTS

WO 02082999 A1 10/2002
WO 2005066868 A2 7/2005

OTHER PUBLICATIONS

Sep. 8, 2016, International Search Report of the International Searching Authority from the U.S. Receiving Office, in PCT/US2016/037439, which is the international application to this U.S. application.

(Continued)

*Primary Examiner* — Andy Rao
*Assistant Examiner* — Zaihan Jiang
(74) *Attorney, Agent, or Firm* — Kilpatrick Townsend & Stockton LLP

(57) ABSTRACT

Remote biometric monitoring systems may include a digital camera having a digital sensor, a processor, and a memory, all enclosed in a common housing. The processor of the camera may locally execute one or more algorithms to perform computer vision analysis of captured images of a sleeping subject, thereby determining an activity state of the subject. The activity state may include a sleep state. One or more environmental control devices may be adjusted automatically by the system based at least in part on the activity state.

21 Claims, 12 Drawing Sheets

(51) Int. Cl.
  *G06K 9/62* (2006.01)
  *A61B 5/0205* (2006.01)
  *H04N 7/18* (2006.01)
  *H04N 5/225* (2006.01)
  *A61B 5/024* (2006.01)
  *A61B 5/08* (2006.01)
  *H04N 5/33* (2006.01)

(52) U.S. Cl.
  CPC ........ *A61B 5/1113* (2013.01); *G06K 9/00369* (2013.01); *G06K 9/00885* (2013.01); *H04N 5/2252* (2013.01); *H04N 7/183* (2013.01); *A61B 5/024* (2013.01); *A61B 5/0816* (2013.01); *H04N 5/33* (2013.01)

(58) Field of Classification Search
  USPC .......................................................... 348/77
  See application file for complete search history.

(56) References Cited

U.S. PATENT DOCUMENTS

| | | | |
|---|---|---|---|
| 7,774,052 B2 * | 8/2010 | Burton | A61B 5/0476 600/544 |
| 8,628,453 B2 * | 1/2014 | Balakrishnan | A63B 71/0686 482/1 |
| 8,907,287 B2 * | 12/2014 | Vanderpohl | A61B 5/0077 250/349 |
| 9,375,142 B2 * | 6/2016 | Schultz | A61B 5/0002 |
| 2013/0245465 A1 | 9/2013 | Kasama | |
| 2014/0072190 A1 | 3/2014 | Wu et al. | |
| 2015/0288877 A1 | 10/2015 | Glazer | |

OTHER PUBLICATIONS

Sep. 8, 2016, Written Opinion of the International Searching Authority from the U.S. Receiving Office, in PCT/US2016/037439, which is the international application to this U.S. application.

* cited by examiner

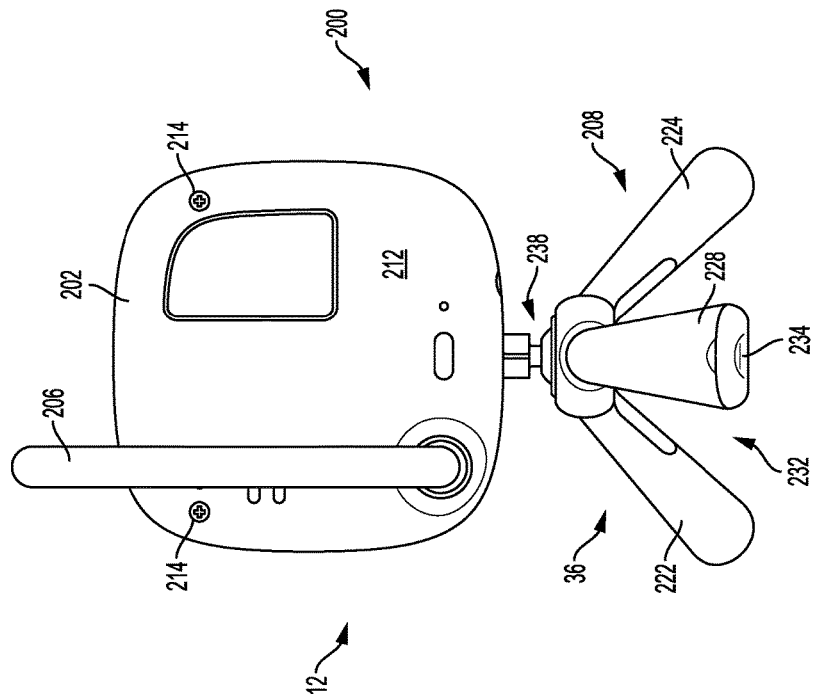
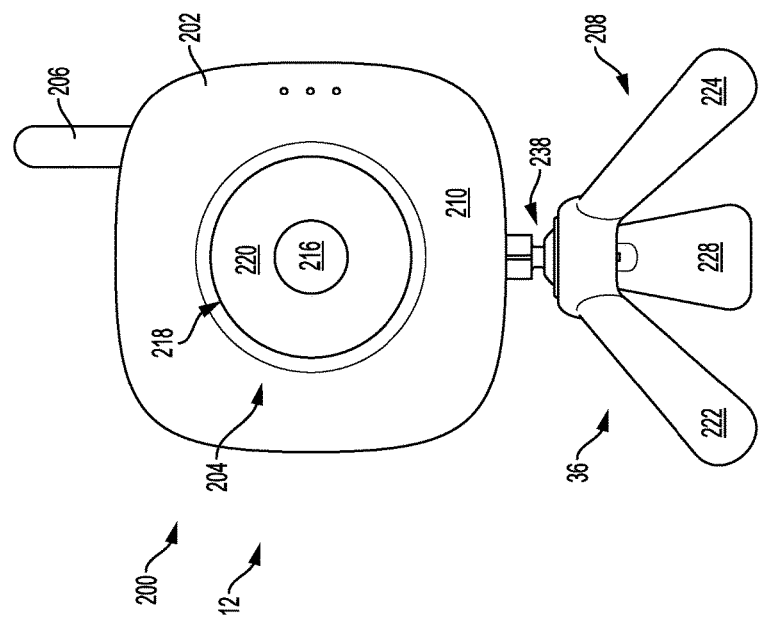
FIG. 6
FIG. 7

REMOTE BIOMETRIC MONITORING SYSTEM

CROSS-REFERENCES

This application claims priority from U.S. Provisional Patent Application Ser. No. 62/175,613, filed Jun. 15, 2015, which is hereby incorporated by reference in its entirety for all purposes.

INTRODUCTION

Baby monitors, including video monitors, are well known. However, such devices typically operate simply by capturing images and/or sounds and transmitting them to a remote location, where a parent or caregiver is located. Such monitors typically do not analyze the images or sounds to determine if the child needs assistance, but rather this analysis is performed on the unprocessed data by the parent or caregiver. For this reason, existing child monitors typically do not include biometric sensors or advanced analysis tools. Furthermore, existing monitors can be relatively intrusive, due to the need to broadcast all of the information captured in the vicinity of the child. Accordingly, there is a need for a child monitoring system that can capture more subtle or additional information about a monitored child, analyze the captured information and interpret or partially interpret it for a remote user, and do so in a manner that is relatively less invasive than existing child monitoring systems.

Biometric health monitoring systems are well known in hospital and clinical health care facilities. Typically, such monitoring systems include various sensors that are physically attached to a patient, and a feature that alerts a medical professional, such as a nurse or doctor, if the patient's vital signs fall outside of an acceptable range. Systems of this type can also be adapted for home use, but typically still require the physical attachment of various sensors to the patient. Therefore, there is a need for health monitoring systems that can monitor and analyze various biometric parameters of a person, and alert a remote caregiver, without requiring the invasive attachment of multiple sensors to the monitored person.

SUMMARY

The remote biometric monitoring systems described herein overcome the problems described above by, for example, determining biometric parameters of a subject noninvasively, using computer vision analysis of images captured by a digital camera.

In some embodiments, a system for remotely monitoring a sleeping subject may include a digital camera configured to capture images of a subject, the camera including a digital image sensor, one or more processors in communication with the digital image sensor, and a memory, wherein the digital image sensor, the one or more processors, and the memory are enclosed in a same housing; an environmental sensor in communication with the one or more processors of the digital camera, the environmental sensor configured to detect a physical characteristic of a local environment of the subject; an environmental control device in communication with the one or more processors of the digital camera, the environmental control device configured to produce a change in the local environment of the subject; and a set of instructions stored in the memory of the digital camera and executable locally by the one or more processors to: receive a sensed input from the environmental sensor and a plurality of time-sequenced images of the subject from the digital image sensor; determine, using an artificial intelligence module, a position of a body region of the subject in a subset of images of the time-sequenced plurality of images; identify, using the position of the body region determined by the artificial intelligence module to perform a biometric analysis on the plurality of time-sequenced images, an activity state of the subject; and cause a change in the environmental control device based on the sensed input and the activity state of the subject.

In some embodiments, a system for remotely monitoring a sleeping person may include a digital camera configured to capture images of a person, the camera including a digital image sensor, one or more processors in communication with the digital image sensor, and a memory, wherein the digital image sensor, the one or more processors, and the memory are enclosed in a same housing; a remote notification device in communication with a user located out of sight of the person; and a set of instructions stored in the memory of the digital camera and executable locally by the one or more processors to: receive a plurality of time-sequenced images of the person from the digital image sensor; determine, using an artificial intelligence module, a position of a body region of the person in at least one image of the time-sequenced plurality of images; identify, using the position of the body region determined by the artificial intelligence to perform a biometric analysis on the plurality of time-sequenced images, an activity state of the person; and communicate information corresponding to the activity state of the person to the user via the remote notification device.

In some embodiments, a method for remotely monitoring a sleep state of a human subject may include: capturing a plurality of time-sequenced images of a human subject using a digital camera having a digital image sensor, one or more processors in communication with the digital image sensor, and a memory, wherein the digital image sensor, the one or more processors, and the memory are enclosed in a same housing; determining, using the one or more processors to execute a machine intelligence module in the memory of the digital camera, a position of a body region of the subject in at least one image of the time-sequenced plurality of images; identifying, using the one or more processors to execute a biometric analysis on the body region of the plurality of time-sequenced images, an activity state of the subject; and causing a change in a local environment of the subject based at least in part on the activity state of the subject.

Features, functions, and advantages may be achieved independently in various embodiments of the present disclosure, or may be combined in yet other embodiments, further details of which can be seen with reference to the following description and drawings.

BRIEF DESCRIPTION OF THE DRAWINGS

FIG. 6 is a front elevation view of the digital camera of FIG. 5.

FIG. 7 is a rear elevation view of the digital camera of FIG. 5.

DESCRIPTION

Figure 1:
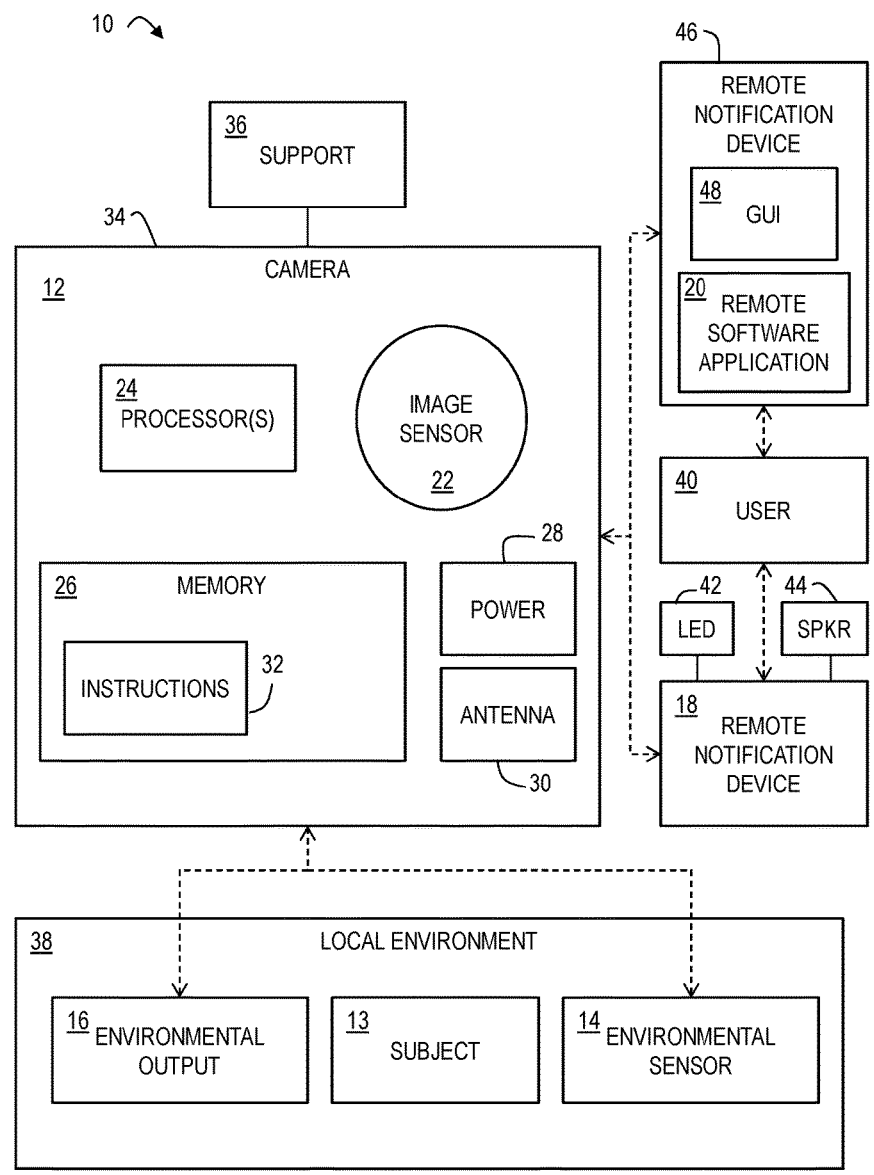
FIG. 1 is a schematic diagram of an illustrative remote biometric monitoring system in accordance with aspects of the present disclosure.

Various aspects and examples of a remote biometric monitoring system, as well as related methods, are described below and illustrated in the associated drawings. Unless otherwise specified, a remote biometric monitoring system according to the present teachings and/or its various components may, but are not required to, contain at least one of the structure, components, functionality, and/or variations described, illustrated, and/or incorporated herein. Furthermore, unless specifically excluded, the process steps, structures, components, functionalities, and/or variations described, illustrated, and/or incorporated herein in connection with the present teachings may be included in other similar devices and methods, including being interchangeable between disclosed embodiments. The following description of various examples is merely illustrative in nature and is in no way intended to limit the disclosure, its application, or uses. Additionally, the advantages provided by the examples and embodiments described below are illustrative in nature and not all examples and embodiments provide the same advantages or the same degree of advantages.

Definitions

The following definitions apply herein, unless otherwise indicated.

"Substantially" means to be essentially conforming to the particular dimension, range, shape, or other aspect modified by the term, such that a feature or component need not conform exactly. For example, a "substantially cylindrical" object means that the object resembles a cylinder, but may have one or more deviations from a true cylinder.

"Comprising," "including," and "having" (and conjugations thereof) are used interchangeably to mean including but not necessarily limited to, and are open-ended terms not intended to exclude additional, unrecited elements or method steps.

Terms such as "first", "second", and "third" are used to distinguish or identify various members of a group, or the like, and are not intended to show serial or numerical limitation.

Overview

In general, a remote biometric monitoring system according to the present teachings may include a digital camera having one or more onboard processors and memory configured to perform computer vision analysis. This analysis may be configured to determine various aspects of the activity (e.g., the activity state) of a human subject. Although the subject may be any age, the subject may typically be a child or infant. Analysis may include determination of sleep state, motion, respiration, heart rate, etc. Machine learning techniques and/or artificial intelligence may be used to analyze images from the digital camera, and biometric and actigraphic data may be ascertained without physically contacting the subject. A remote biometric monitoring system may be configured as a sleep monitoring system. In some examples, all image, actigraphy, and biometric processing is performed locally by the digital camera.

In some examples, a remote biometric monitoring system may be in communication with at least one environmental sensor (e.g., temperature sensor, humidity sensor, microphone) in the local environment of the subject. Data from the environmental sensor(s) may be used to facilitate analysis and/or to determine actions that may be taken. For example, the remote biometric monitoring system may be in communication with an environmental output (e.g., a heating, ventilation, and air conditioning (HVAC) system, dehumidifier, lighting system), such that when a certain activity or activity state is present, the remote biometric monitoring system may cause the environmental output to adjust an aspect of the local environment. In some examples, this adjustment occurs only if the environmental sensor determines that an environmental characteristic is above or below a selected threshold value.

Aspects of remote biometric monitoring systems as taught herein may be embodied as a computer method, computer system, or computer program product. Accordingly, aspects of the remote biometric monitoring system may take the form of an entirely hardware embodiment, an entirely software embodiment (including firmware, resident software, micro-code, and the like), or an embodiment combining software and hardware aspects, all of which may generally be referred to herein as a "circuit," "module," or "system." Furthermore, aspects of the remote biometric monitoring system may take the form of a computer program product embodied in a computer-readable medium (or media) having computer-readable program code/instructions embodied thereon.

Any combination of computer-readable media may be utilized. Computer-readable media can be a computer-readable signal medium and/or a computer-readable storage medium. A computer-readable storage medium may include an electronic, magnetic, optical, electromagnetic, infrared, and/or semiconductor system, apparatus, or device, or any suitable combination of these. More specific examples of a computer-readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, and/or any suitable combination of these and/or the like. In the context of this disclosure, a computer-readable storage medium may include any suitable tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, and/or any suitable combination thereof. A computer-readable signal medium may include any computer-readable medium that is not a computer-readable storage medium and that is capable of communicating, propagating, or transporting a program for use by or in connection with an instruction execution system, apparatus, or device.

Program code embodied on a computer-readable medium may be transmitted using any appropriate medium, including but not limited to wireless, wireline, optical fiber cable, RF, and/or the like, and/or any suitable combination of these.

Computer program code for carrying out operations for aspects of the remote biometric monitoring system may be written in one or any combination of programming languages, including an object-oriented programming language such as Java, Smalltalk, C++, and/or the like, and conventional procedural programming languages, such as C. Mobile apps may be developed using any suitable language, including those previously mentioned, as well as Objective-C, Swift, C#, HTML5, and the like. The program code may execute entirely on a user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), and/or the connection may be made to an external computer (for example, through the Internet using an Internet Service Provider).

Aspects of the remote biometric monitoring system are described below with reference to flowchart illustrations and/or block diagrams of methods, apparatuses, systems, and/or computer program products. Each block and/or combination of blocks in a flowchart and/or block diagram may be implemented by computer program instructions. The computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions can also be stored in a computer-readable medium that can direct a computer, other programmable data processing apparatus, and/or other device to function in a particular manner, such that the instructions stored in the computer-readable medium produce an article of manufacture including instructions which implement the function/act specified in the flowchart and/or block diagram block or blocks.

The computer program instructions can also be loaded onto a computer, other programmable data processing apparatus, and/or other device to cause a series of operational steps to be performed on the device to produce a computer-implemented process such that the instructions which execute on the computer or other programmable apparatus provide processes for implementing the functions/acts specified in the flowchart and/or block diagram block or blocks.

Any flowchart and/or block diagram in the drawings is intended to illustrate the architecture, functionality, and/or operation of possible implementations of systems, methods, and computer program products according to aspects of the remote biometric monitoring system. In this regard, each block may represent a module, segment, or portion of code, which comprises one or more executable instructions for implementing the specified logical function(s). In some implementations, the functions noted in the block may occur out of the order noted in the drawings. For example, two blocks shown in succession may, in fact, be executed substantially concurrently, or the blocks may sometimes be executed in the reverse order, depending upon the functionality involved. Each block and/or combination of blocks may be implemented by special purpose hardware-based systems (or combinations of special purpose hardware and computer instructions) that perform the specified functions or acts.

EXAMPLES, COMPONENTS, AND ALTERNATIVES

The following sections describe selected aspects of exemplary remote biometric monitoring systems, as well as related systems and/or methods. The examples in these sections are intended for illustration and should not be interpreted as limiting the entire scope of the present disclosure. Each section may include one or more distinct embodiments or examples, and/or contextual or related information, function, and/or structure.

Illustrative Remote Biometric Monitoring System

As shown schematically in FIG. 1, this section describes an illustrative remote biometric monitoring system 10. System 10 is an example of the remote biometric monitoring system described in the overview above.

System 10 includes a digital camera 12 configured to capture images of a subject 13 (e.g., a human subject, a person). Digital camera 12 may be in communication with an environmental sensor 14, an environmental control device 16, a dedicated remote notification device 18, and/or a remote software application 20. For example, digital camera 12 may be in wireless communication with one or more of these devices. For example, this communication may include a local area network (LAN). In some examples, this communication may include a wireless protocol (e.g., WiFi or Bluetooth®).

Digital camera 12 may include any suitable components configured to capture a plurality of time-sequenced images and to perform computer vision analysis on the images as described below. In some examples, digital camera 12 includes a video camera. As depicted in FIG. 1, digital camera 12 may include an image sensor 22, a processor 24, a memory 26, a power supply 28, and a communications module 30. Digital camera 12 is an example of a data processing system. Data processing systems are described further below, with respect to FIG. 12.

Image sensor 22 may include any suitable digital image sensor configured to capture images in the visible and/or infrared (IR) spectrum. For example, image sensor 22 may include a CMOS sensor such as those typically found in smart phones and/or tablets. Suitable image sensors may include those sold as the Omnivision OV4682 or the 3-megapixel Aptina AR0330. Infrared illumination may be provided to enhance night vision.

Processor 24 may include one or more of any suitable microprocessor, chip, or system on a chip (SOC), including a central processing unit (CPU), graphical processing unit (GPU), and/or the like, configured to execute instructions to perform the computer vision analyses described herein. For example, suitable processors 24 may include those sold as the Nvidia Tegra K1 or the Qualcomm Snapdragon 410.

Memory 26 may include any suitable storage device or devices in communication with processor 24 and configured to retrievably store digital information. For example, memory 26 may include random access memory (RAM) (e.g., SDRAM), one or more solid state drives (SSDs), a secure digital (SD) card, and/or the like, or any combination of these. See description of data processing systems below for further discussion of digital memory. Memory 26 includes one or more sets of instructions 32 (e.g., computer programs, code, module(s)) stored in the memory and executable by processor 24.

Power supply 28 may include any suitable power management device configured to provide adequate and stable power to camera 12. Power input 28 may include a power management integrated circuit (PMIC), a power source (e.g., a battery, a power cord for accessing household outlet power), an adapter (e.g., an AC to DC adapter or converter), and/or the like, or any combination of these.

Communications module 30 may include any suitable device(s) configured to provide wireless communication with one or more external devices. For example, module 30 may include a transmitter, a receiver, an antenna, a universal asynchronous receiver/transmitter (UART), and/or the like, or any combination of these. Module 30 may be configured to operate in accordance with a wireless standard or protocol, such as WiFi, Bluetooth®, Bluetooth Low Energy (LE), and/or the like, or any combination of these.

Some or all of the components of camera 12 may be enclosed in a same (i.e., common) housing 34. For example, image sensor 22, processor 24, and memory 26 may be enclosed in housing 34. In some examples, the sensor, processor, and memory are mounted on a printed circuit board (PCB) enclosed by the housing. Housing 34 may include a structural and/or protective enclosure configured to package the components. In some examples, housing 34 includes a hard plastic shell. In some examples, housing 34 includes an access door.

Camera 12 may be mounted or otherwise coupled to a support 36. Support 36 may include any suitable structure configured to hold camera 12 in a selected orientation on or against a selected support surface. In some examples, support 36 may be unitary with housing 34. In some examples, support 36 may include an adjustable support, e.g., a tripod having independently length-adjustable legs. In some examples, support 36 may include a stand, a pedestal, a hanger, a bracket, a cage, one or more articulating or articulatable joints, and/or the like, or any combination of these.

Environmental sensor 14 may include any suitable sensor (e.g., transducer) in communication with camera 12 (e.g., with processor 24 via communications module 30) and configured to detect a physical characteristic of a local environment 38 of subject 13. For example, environmental sensor 14 may include a temperature sensor, a humidity sensor, an air quality sensor, a microphone, a light sensor, and/or any other sensor related to the objective or subjective experience of subject 13. Remote biometric monitoring system 10 may be used to monitor the sleep of subject 13. Accordingly, environmental sensor 14 may relate to a quality of sleep (e.g., comfortable temperature), and/or to an correlated indicator of sleep quality (e.g., snoring noises). Sensor 14 may be in communication with camera 12, by hardwire or wirelessly, to provide an input corresponding to the measured environmental characteristic (e.g., sound level, temperature, particulate count, humidity, etc.).

Environmental control device 16 may include any suitable device in communication with camera 12 (e.g., with processor 24 via communications module 30) and configured to modify, adjust, or otherwise produce a change in local environment 38. For example, environmental control device 16 may include one or more of the following devices (or controllers therefor): an audio speaker, a heater, a cooler, an HVAC device, a humidifier, a dehumidifier, a white noise generator, a fan, a lamp (e.g., a dimmable lamp, a night light), a recorded music or spoken word player, and/or the like. In general, as mentioned above, system 10 may be configured to adjust, control, enable, or disable the environmental control device in response to selected conditions. For example, if the system determines that a respiration pattern of subject 13 is labored, processor 24 may cause environmental control device 16 to adjust a humidity level in local environment 28.

Dedicated remote notification device 18 may include any suitable device in communication with camera 12 (e.g., with processor 24 of camera 12 via communications module 30 or a suitable input/output port) and configured to provide information relating to biometric parameters of subject 13 to a user 40 located out of sight of the subject. In some examples, remote notification device 18 includes an ambient display device having one or more light emitting diodes (LEDs) 42 and/or an audio speaker 44. Remote notification device 18 may, for example, include a portable device configured to receive commands wirelessly from the processor and to provide information to the user in the form of light, sound, and/or vibration. For example, remote notification device 18 may be configured to display a changing light pattern corresponding to a breathing pattern of subject 13. In some examples, remote notification device 18 may be configured to alert user 40 in response to one or more predetermined alarm conditions regarding subject 13. Alarm conditions may include breathing problems, coughing, inability of the system to locate the subject in the images, sensed environmental characteristics outside of allowable limits, etc.

Remote software application 20 may include any suitable computer code or application capable of running (e.g., executing) on a computing device 46 (e.g., portable device, tablet, smart phone, and/or computer) of user 40, and configured to receive information from processor 24 and to display the information on a graphical user interface (GUI) (e.g., on a display screen) of device 46. Device 46 may be an example of a data processing system, as described further below with respect to FIG. 12.

Remote software application 20 may include an app for use on a portable device, such as a tablet, and/or a software application for use on a non-portable device, such as a desktop computer. Application 20 may include features similar to those of remote notification device 18, such as displaying patterns, emitting sounds, and providing alerts in response to information received from camera 12. In some examples, application 20 may include a display of an activity timeline or history relating to sleep or other activity states of subject 13. In some examples, application 20 may include a display of images from camera 12 (e.g., a live video stream and/or selected playable video clips).

In some examples, device 46 may be described as a remote notification device, and may include aspects that are substantially functionally identical to notification device 18. For example, one or both of devices 18 and 46 may be present, and both may function as remote notification devices for the user. Either or both may be referred to as a remote notification device, the distinction being that device 18 is a dedicated device providing ambient displays and alerts, while device 46 may be a general purpose device (e.g., a smart phone) programmed to communicate the same or greater information, possibly with additional features or sophistication (e.g., using GUI 48).

In some examples, subject 13 may be a child or infant. In some examples, user 40 may include a parent or caregiver of subject 13. For example, a parent of a sleeping child may utilize remote biometric monitoring system 10 to monitor the sleep state, sleep quality, and/or breathing characteristics of the child from another room and/or over time.

Illustrative Computer Vision Analysis

Figure 2:
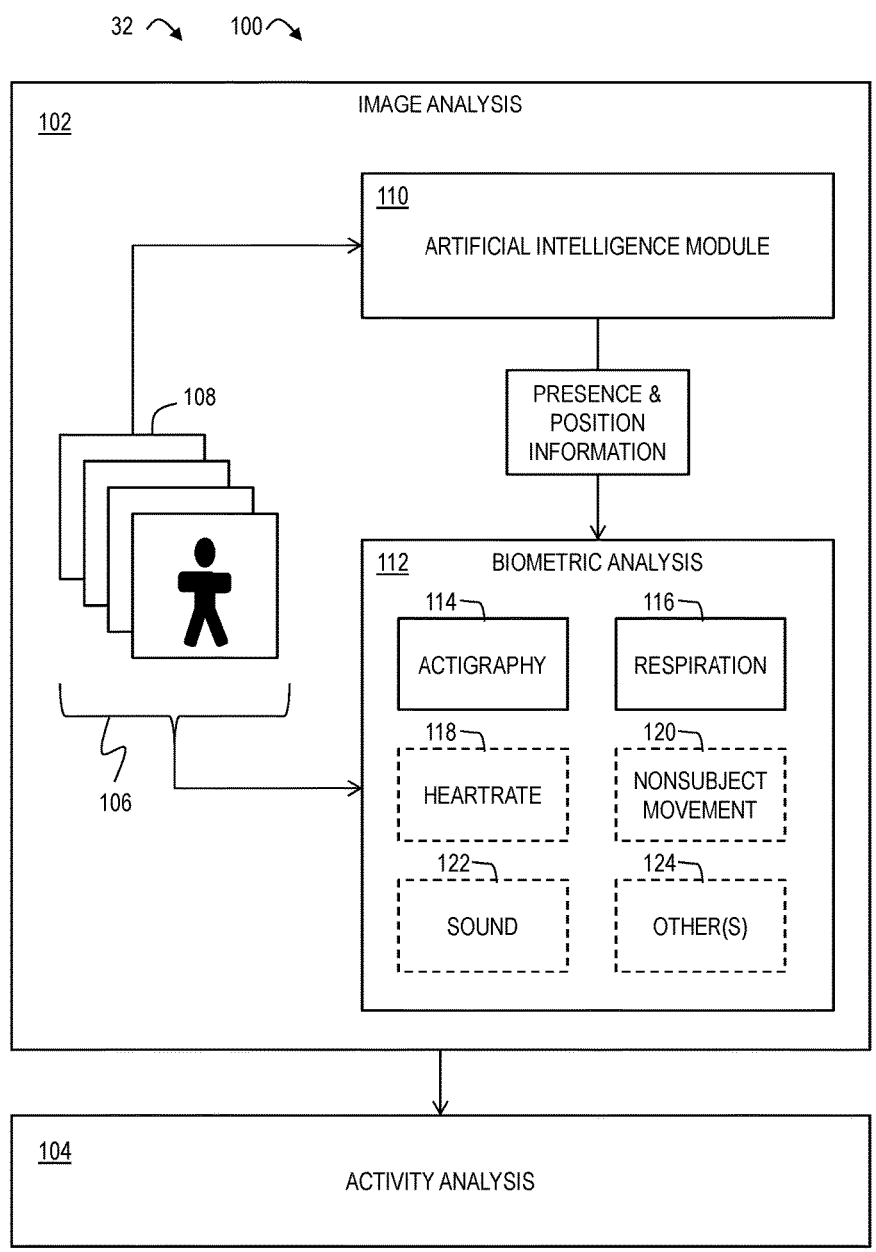
FIG. 2 is a schematic diagram of an illustrative computer vision analysis algorithm in accordance with aspects of the present disclosure.
Figure 3:
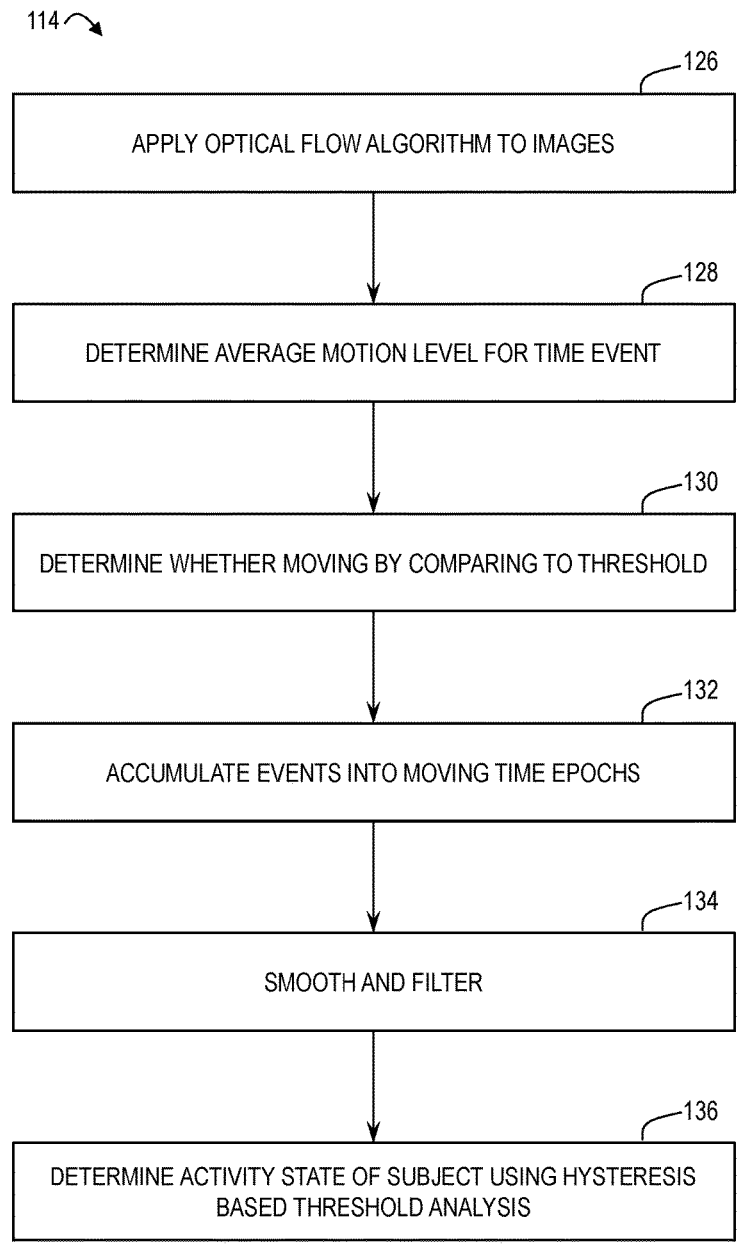
FIG. 3 is a flow chart depicting steps in an illustrative actigraphic analysis algorithm suitable for use in the algorithm of FIG. 2.
Figure 4:
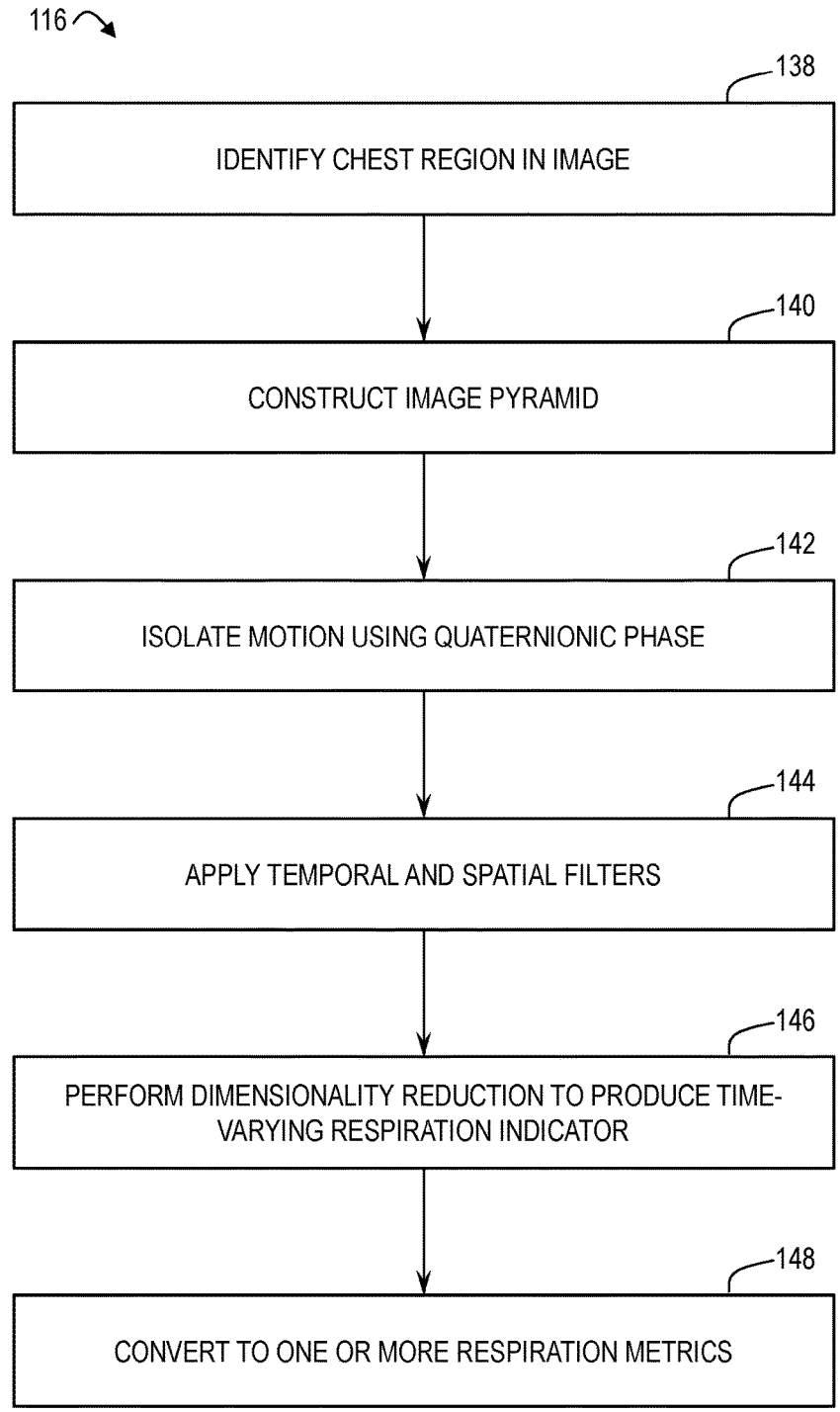
FIG. 4 is a flow chart depicting steps in an illustrative respiration analysis algorithm suitable for use in the algorithm of FIG. 2.
Figure 5:
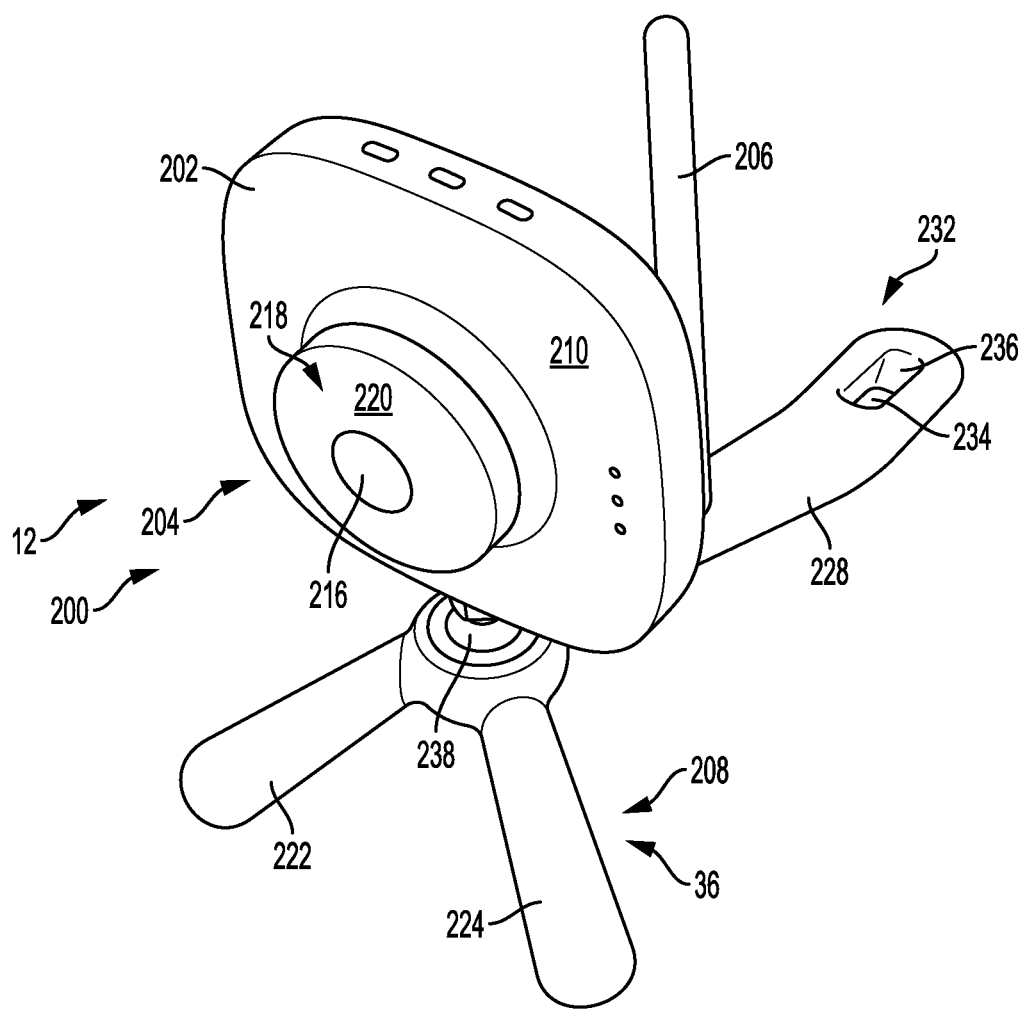
FIG. 5 is an oblique isometric view of an illustrative digital camera suitable for use in the system of FIG. 1.
Figure 8:
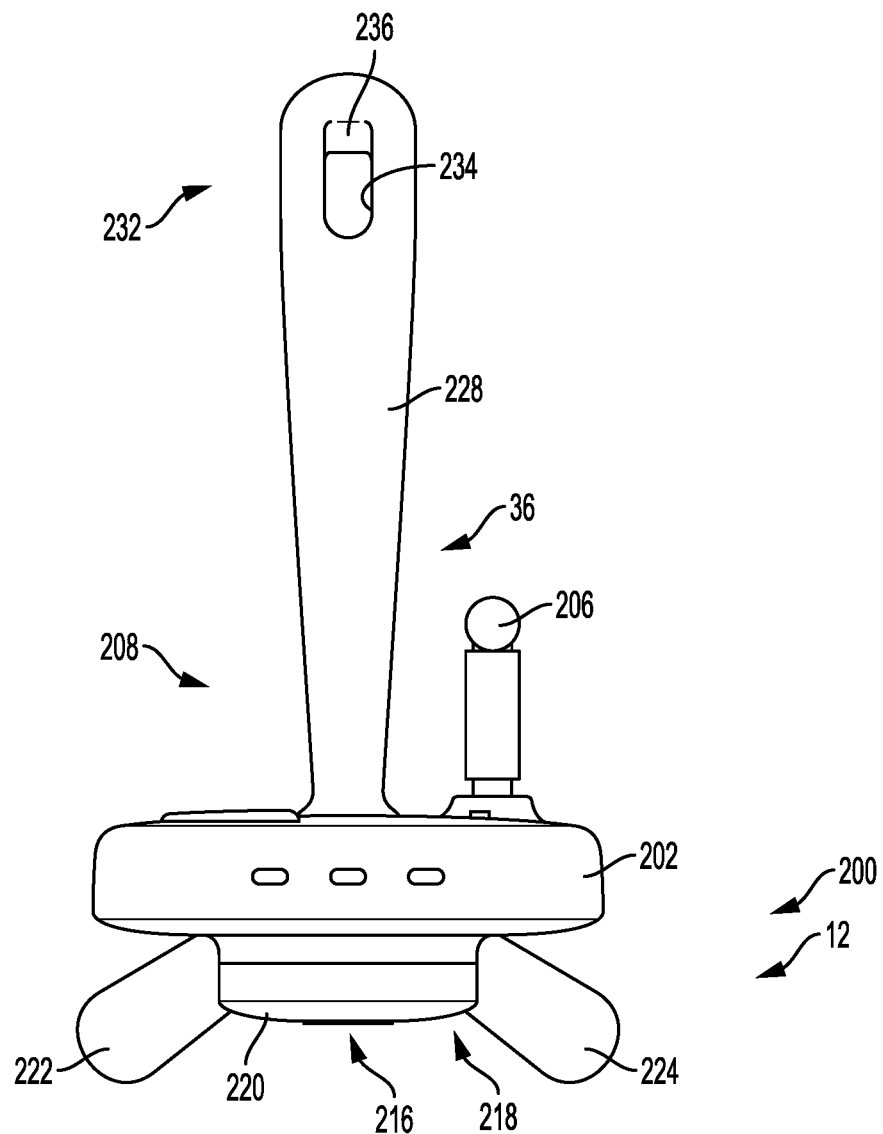
FIG. 8 is a top plan view of the digital camera of FIG. 5.
Figure 9:
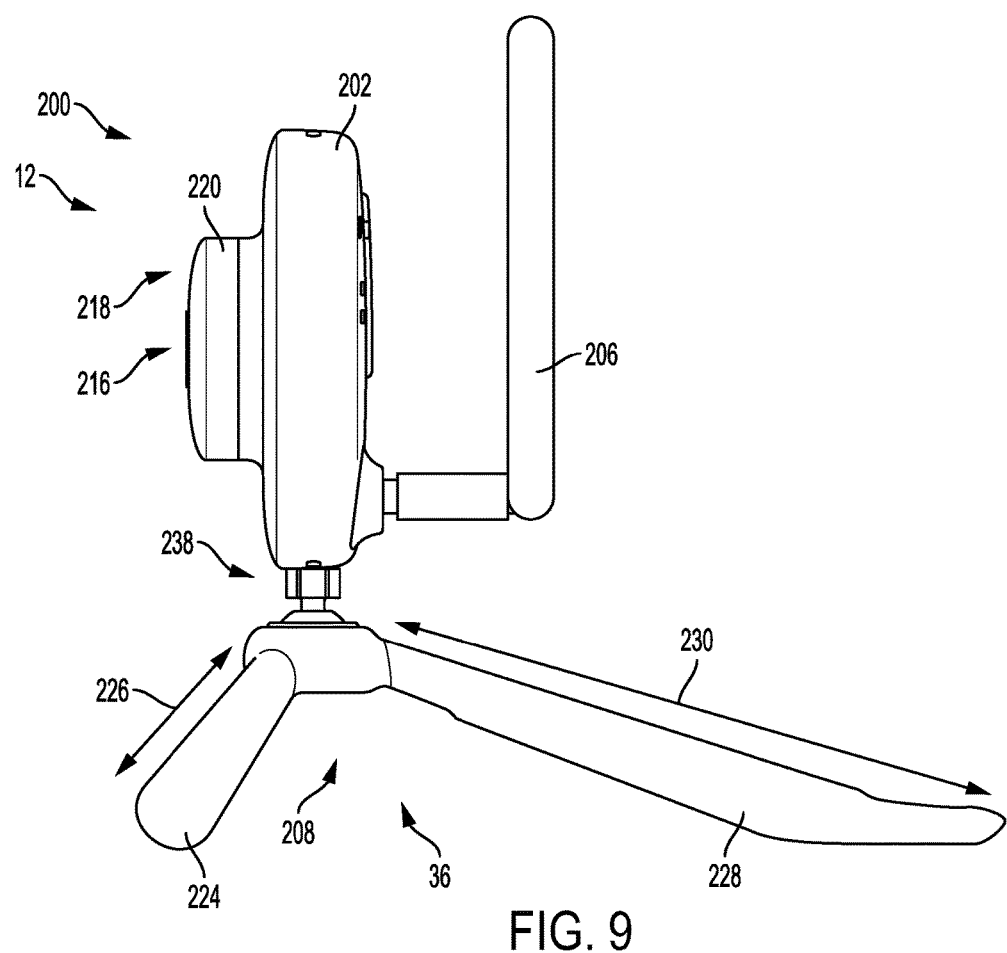
FIG. 9 is a side elevation view of the digital camera of FIG. 5.

As shown in FIGS. 2-4, this section describes an illustrative computer vision analysis algorithm 100. Algorithm 100 is an example of instructions 32 that are executable by processor 24 of camera 12, as described above. Algorithm 100 and related methods are described below as being executed by system 10. Any suitable example or embodiment of system 10 may be used.

With reference to FIG. 2, algorithm 100 includes an image analysis 102 and an activity analysis 104. In general, the processor(s) of remote biometric monitoring system 10 determine the presence and position of a subject in the images from the camera sensor, and perform various analyses on the sequenced images to determine, e.g., movement, respiration, heart rate, and/or other biometric aspects of the subject. This information is then utilized to determine an activity state of the subject, e.g., awake or asleep.

Accordingly, a plurality of time-sequenced images 106 is received from image sensor 22. A subset of the images, e.g., one of the images 108, is provided to an artificial intelligence (AI) module 110, also referred to as a machine learning or machine intelligence module. AI module 110 may include a neural network (NN), e.g., a convolutional neural network (CNN), trained to determine whether a human subject is present in the image and to determine the skeletal posture of the subject. Any suitable AI method and/or neural network may be implemented, e.g., using known techniques. For example, a fully convolutional neural network for image recognition may be implemented using the TensorFlow machine intelligence library.

The NN may determine a respective position (e.g., X, Y coordinates) of one or more body regions of the subject, such as the torso, head, neck, and/or waist. Based on the positions of the one or more body regions, the NN may provide a bounding box generally identifying where the subject is located in the image. The NN may also provide a confidence level with respect to its determination that a subject is present in the image. The presence determination, confidence level, body region locations, and/or bounding box information may then be provided to a biometric analysis module 112.

Biometric analysis module 112 may include any suitable routines and/or algorithms configured to perform first-level measurements of biological activities of the subject based on images 106. The results of the biometric analysis may be used to determine an activity state of the subject and/or to drive displays or communication of the measurements (e.g., displaying pulse information). Examples of biometric algorithms of the biometric analysis module include an actigraphic analysis algorithm 114, a respiration algorithm 116, a heart rate algorithm 118, a non-subject movement algorithm 120, a sound correlation algorithm 122, and others 124. In some examples, any of these biometric algorithms may be present, absent, or selectively enabled or disabled, e.g., by a user. In the example shown in FIG. 2, actigraphic analysis algorithm 114 and respiration algorithm 116 are enabled.

Actigraphic analysis algorithm 114 may include any steps or operations configured to determine, from the series of images, whether the subject is moving. An example of an actigraphic analysis algorithm is illustrated in FIG. 3. FIG. 3 is a flowchart illustrating steps performed in an illustrative method, and may not recite the complete process or all steps of the method. Although various steps of algorithm 114 are described below and depicted in FIG. 3, the steps need not necessarily all be performed, and in some cases may be performed in a different order than the order shown.

Actigraphic analysis algorithm 114 may be applied to raw, uncompressed versions of images 106. This may be advantageous, for example, due to the sensitive nature of optical flow methods described below. Any loss in fidelity or information due to compression or transmission may greatly affect the accuracy and feasibility of the algorithm. Accordingly, systems according to the present teachings will typically perform algorithm 114 on-camera (i.e., locally). In some examples, all algorithms of computer vision analysis algorithm 100 are performed locally.

At step 126 of algorithm 114, an optical flow algorithm may be applied to images 106. Any suitable optical flow algorithm may be utilized. For example, a dense optical flow algorithm (e.g., Farneback's) may be used to analyze all pixels of the image. In some examples, a sparse optical flow algorithm (e.g., Lucas-Kanade) may be used to analyze a subset of pixels. For example, one or more specific body regions of interest may be analyzed rather than the entire image.

At step 128 of algorithm 114, the average motion level for a selected time event may be determined. For example, a time event may be defined as a one-second interval. Average level of motion may be calculated for this time interval, based on the optical flow. In some examples, the average motion may be determined only for the region in which the subject is located. For example, the average motion may be calculated for the area within the bounding box provided by the AI module, or based on that information. In some examples, motion may be filtered, such as by ignoring high-movement areas.

At step 130 of algorithm 114, it may be determined whether the subject is moving by comparing the average motion to a selected threshold. For example, if the average motion exceeds a certain value, it may be assumed that the subject is moving. This step may produce a binary result, i.e., a determination of "moving" or "not moving." In some examples, more than two categories of movement may be used, such as by categorizing movement into multiple levels (e.g., low, medium, high).

At step 132 of algorithm 114, the results of each event (e.g., one-second interval) may be accumulated into longer time periods referred to as epochs. For example, a moving thirty-second epoch may be constructed. In some examples, each event is centered in a plus or minus fifteen second interval. A level of movement may then be determined for each epoch.

At step 134 of algorithm 114, the epoch-based movement determinations may be smoothed and filtered as desired. In some examples, inertia may be mathematically added to the system.

At step 136 of algorithm 114, the activity state of the subject may be determined, based on a threshold analysis. Transitions between states may be determined by incorporating hysteresis. For example, activity states may include asleep or awake. The asleep state may be further subdivided into still sleep and active sleep. In some examples, some or all of this step's analysis may be performed in activity analysis module 104.

Respiration algorithm 116 may include any steps or operations configured to determine, from the series of images, a breathing pattern of the subject. An example of a respiration algorithm is illustrated in FIG. 4. FIG. 4 is a flowchart illustrating steps performed in an illustrative method, and may not recite the complete process or all steps of the method. Although various steps of algorithm 116 are described below and depicted in FIG. 4, the steps need not necessarily all be performed, and in some cases may be performed in a different order than the order shown.

At step 138 of algorithm 116, a chest region of the subject may be identified in images 106. This may be performed by AI module 110, or by the present algorithm using known computer vision techniques.

At step 140 of algorithm 116, a complex image pyramid may be constructed for each frame of the video feed (i.e., of images 106). Construction of image pyramids is a known preprocessing technique in the computer vision field.

At step 142 of algorithm 116, motion between frames may be isolated using the quaternionic phase information from the image pyramids.

At step 144 of algorithm 116, filters may be applied to isolate motion caused by respiration. A Butterworth filter (or other suitable filter) may be applied to temporally filter for the general range of frequencies involved in respiratory movement. A Gaussian blur filter (or other suitable filter) may be applied to filter spatially. An amplitude weighting filter may be applied to improve signal-to-noise ratio.

At step 146 of algorithm 116, a dimensionality reduction is performed on the filtered video feed, to obtain a single, time-varying number corresponding to respiration of the subject. For example, a principle component analysis (PCA) may be performed on a plurality of regions of the image (e.g., five regions), to produce the time-varying indicator. The respiration indicator may be a number that ramps up and down over time, coinciding with the depth and length of the subject's breaths.

At step 148 of algorithm 116, the information from step 146 may be converted to one or more respiration metrics, such as respiration rate, breathing depth, inhalation/exhalation duration, and/or regularity.

Heart rate algorithm 118 may include any suitable steps, and may be substantially similar to algorithm 116. However, rather than analyzing motion of the chest region, motion may be analyzed with respect to the subject's head and filtered for heart rate frequencies. Alternatively or additionally, heart rate algorithm 118 may include analysis regarding the tone of the image. Tonal analysis may be appropriate, because blood flow through the head region subtly changes the skin color of the subject in time with the heart rate.

Non-subject motion algorithm 120 may include any suitable steps, and may be substantially similar to actigraphic algorithm 114. However, rather than analyzing motion within the bounding box, algorithm 120 may analyze motion outside of the bounding box. This information may be used, for example, to determine whether another individual (e.g., a parent, sibling, or pet) is present in the images. Suitable thresholds and other aspects may be utilized to determine whether a parental visit has occurred, and/or to trigger other events, such as alarms or to flag a video clip for later review by the user.

Sound algorithm 122 may include any suitable steps, and may include receiving sound information from a microphone monitoring local environment 38 of subject 13. In some examples, sound information may be fed through an artificial intelligence module configured to identify selected sound patterns, such as crying or coughing. In some examples, other methods may be used, such as sound volume and/or sound variation analysis. Sound-based information may be used independently and/or alongside image analysis techniques to correlate determinations such as movement level and respiration characteristics.

In general, biometric analysis using one or more of the above algorithms is continuously performed and is generally dependent on valid information regarding the location of subject 13 in images 106. Accordingly, presence and position analysis using AI module 110 may be performed periodically (e.g., every 20-40 seconds) and/or whenever the biometric analysis determines that the subject's position is no longer adequately certain. This may occur, for example, when actigraphic algorithm 114 determines that subject movement has exceeded a temporal or spatial limit.

Activity analysis 104 may overlap with biometric analysis 112. However, activity analysis 104 in general refers to the use of biometric information from module 112 to determine an activity state of subject 13 and/or to process correlated or supplemental information. As mentioned above, certain activity states may be determined by one or more of the algorithms of biometric module 112. Activity analysis module 104 may perform higher level analysis to correlate the state information using other data, to determine whether other actions should be triggered, and/or to combine outputs of multiple biometric algorithms to improve specificity and/or confidence regarding the activity state of the subject. For example, by combining the results of the actigraphy and respiration algorithms, sleep states can be determined with greater granularity and/or accuracy than by actigraphy alone. For example, based on the two algorithms, activity analysis 104 may determine whether the subject is in a rapid eye movement (REM) sleep state, a deep sleep state, or a light sleep state.

Activity analysis 104 may compare information from various sources to make determinations regarding activity state and/or to trigger actions. For example, activity analysis 104 may receive activity state information from the actigraphic analysis algorithm indicating that the subject is awake. Sound information from sound algorithm 122 and/or respiration information from respiration algorithm 116 may be used to determine that the subject is experiencing labored breathing or a coughing event. This determination may trigger a response by system 10 to increase a humidity level in local environment 38 using a humidity control device (an example of device 16). The determination may also trigger a display or alarm on remote notification device 18 and/or 46.

Illustrative Camera and Support

As shown in FIGS. 5-9, this section describes an illustrative camera 200. Camera 200 is an example of digital camera 12, described above, and may be suitable for use in system 10. Accordingly, camera 200 includes the features described with respect to camera 12. Further details and specific embodiments of various aspects of the camera are described below and shown in the drawings.

Camera 200 includes an outer housing 202, a lens assembly 204, and an antenna 206, and is articulatably coupled to a support 208 (also referred to as a stand). Outer housing 202 is an example of housing 34, and includes a rigid plastic shell enclosing internal components (not shown), such as the camera's image sensor, processor, and memory, all of which are mounted on a PCB. Outer housing 202 may include multiple portions, which may be secured together and/or to one or more internal structures. For example, a front portion 210 and a rear portion 212 of outer housing 202 may be held together (and/or to an internal structure or frame) by screws 214.

Lens assembly 204 may protrude from the front portion of housing 202, and may include a lens 216 and an illumination ring 218. Lens 216 may include any suitable optical focusing device configured to focus incoming images onto the image sensor of the camera. Camera 200 may be capable of visible light, low light, and infrared (IR) imagery. Accordingly, illumination ring 218 may include an IR-transparent cover 220 and an underlying plurality of IR light emitting diodes (LEDs) arranged around the lens. Illumination ring 218 may provide IR illumination of the subject when camera 200 is operating in IR (e.g., night vision) mode.

Antenna 206 may include any suitable antenna configured to transmit and receive wireless signals, e.g., using a WiFi protocol. Antenna 206 may be pivotable, and may be in communication with the communications module of camera 200. In some examples, antenna 206 is internal to the camera, e.g., entirely enclosed within housing 202.

Support 208 is a tripod configured to stably support camera 200. Support 208 is configured to be versatile, supporting the camera in the manner of a standard tripod when on a substantially horizontal support surface (e.g., a shelf), and as a hanging bracket when mounted on a non-horizontal surface (e.g., a wall). In general, camera 200 should be placed in a position where the camera's field of view will be likely to encompass the subject and his or her immediate surroundings (e.g., a bed or crib). Accordingly, the camera may need to be mounted high enough to "see" over the edge or side of a crib. Support 208 facilitates this disposition of the camera by having a leg configuration and mounting aperture that enable wall mounting on a simple hook commonly used in homes.

Specifically, support 208 includes a pair of forward-projecting short legs 222, 224 each having a first permanent length 226, and a rearward-projecting long leg 228 having a second permanent length 230. As shown in FIGS. 5-9, length 230 may be at least fifty percent longer than length 226. In this specific example, long leg 228 is approximately twice as long as each of short legs 222 and 224. This arrangement allows support 208 to have a low, stable profile suitable for support on either a flat surface or a wall.

Furthermore, long leg 228 of the tripod may include a hook interface 232, such that the digital camera can be hung by hook interface 232 on a hook protruding from a substantially vertical support surface. Hook interface 232 may comprise an aperture 234 in a distal end portion of the long leg. Aperture 234 may include a ramped surface 236 creating a wedge-like interface suitable for mating with a typical wall hook. When hung in this fashion, the pair of short legs will provide a stabilizing standoff against the support surface. See FIG. 10. In some examples, aperture 234 may be a through-hole. In some examples, aperture 234 may be a recess in the leg.

Support 208 may further include a ball joint 238 for connecting camera 200 to the support and configured to permit selective orientation of the camera with respect to support 208. As described above, support 208 may be placed on or mounted on a surface having a certain orientation (e.g., horizontal or vertical). However, camera 200 may need to be pointed in a specific direction to capture images of the subject. Accordingly, camera 200 may be pivoted on ball joint 238. Any suitable ball joint or other pivotable joint may be used.

Illustrative Arrangement of Components

Figure 10:
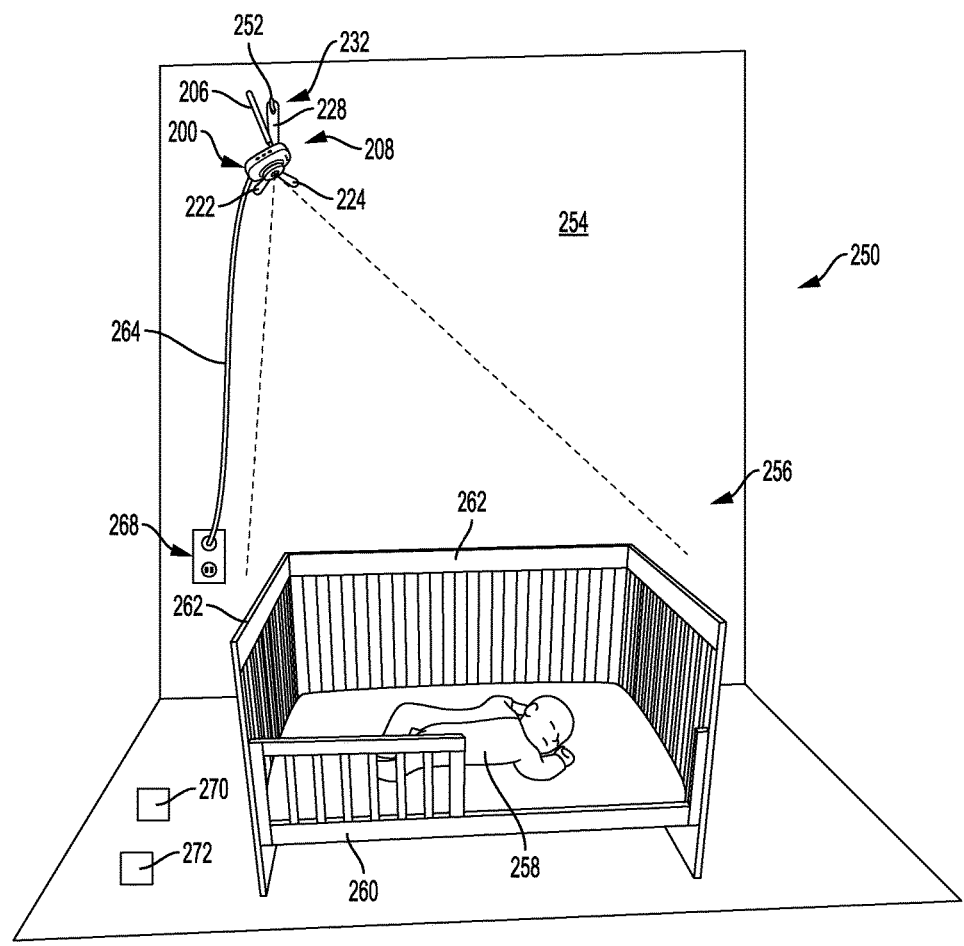
FIG. 10 is a partially schematic view of selected components of an illustrative remote biometric monitoring system in accordance with aspects of the present disclosure.

As shown in FIG. 10, this section describes aspects of an illustrative remote biometric monitoring system 250. System 250 is an example of system 10, described above, and incorporates camera 200.

System 250 includes camera 200, hanging on a hook 252 mounted on a substantially vertical wall 254 of a local environment 256 (e.g., a room). A subject 258 is reclining in a bed 260 having one or more side portions 262. Camera 200 is mounted at a relatively high vantage point (e.g., approximately six feet above the floor) to allow the camera to see over side portions 262 and capture images of subject 258.

A power cord 264 connects camera 200 to a power outlet 268. An environmental sensor 270 is present in environment 256, as is an environmental control device 272, both of which are in wireless communication with camera 200. In this example, sensor 270 may be a microphone, and environmental control device 272 may be a white noise generator. In some examples, the microphone may be integrated into camera 200 or into the white noise generator.

Illustrative Method

Figure 11:
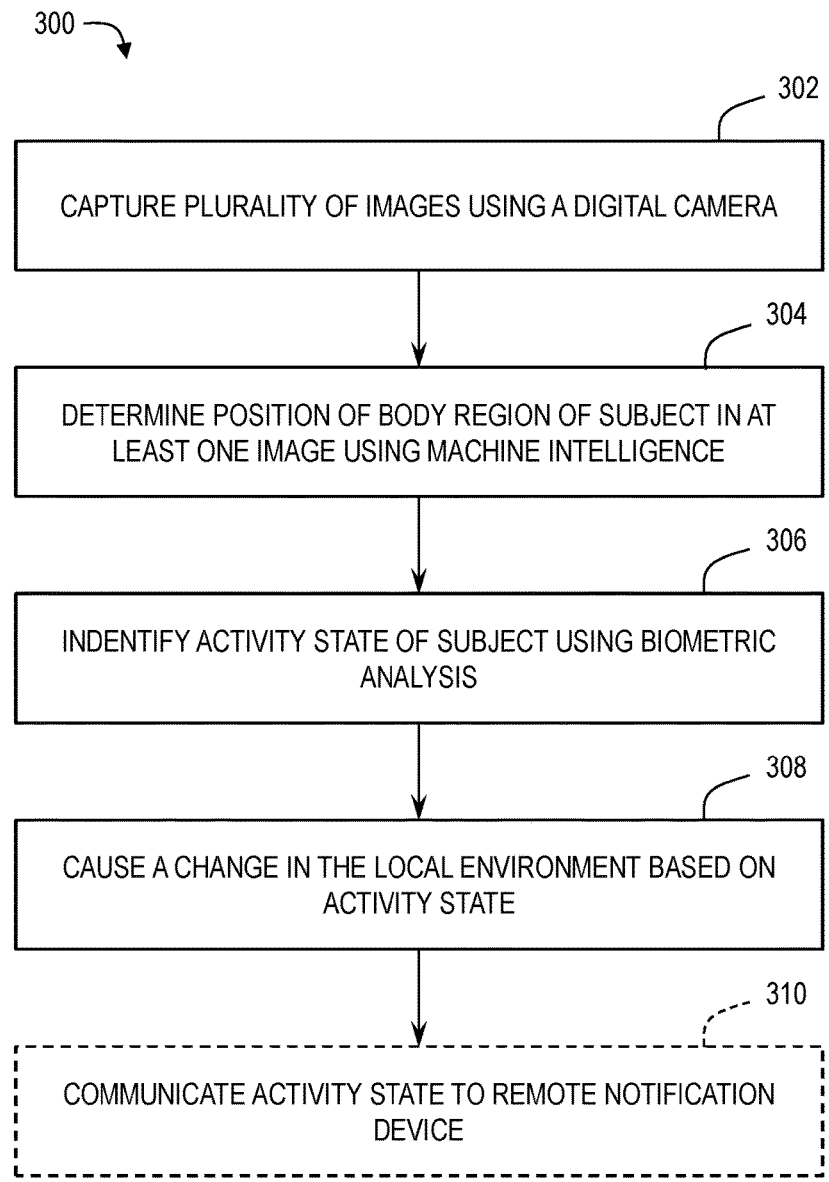
FIG. 11 is a flow chart depicting steps in an illustrative method for remotely monitoring a sleep state of a human subject, in accordance with aspects of the present disclosure.

This section describes steps of an illustrative method for remotely monitoring a sleep state of a human subject; see FIG. 11. Aspects of remote biometric monitoring systems according to the present teachings may be utilized in the method steps described below. Where appropriate, reference may be made to previously described components and systems that may be used in carrying out each step. These references are for illustration, and are not intended to limit the possible ways of carrying out any particular step of the method.

FIG. 11 is a flowchart illustrating steps performed in an illustrative method, and may not recite the complete process or all steps of the method. FIG. 11 depicts multiple steps of a method, generally indicated at 300, which may be performed in conjunction with systems and methods described elsewhere in the present disclosure. Although various steps of method 300 are described below and depicted in FIG. 11, the steps need not necessarily all be performed, and in some cases may be performed in a different order than the order shown.

Step 302 of method 300 includes capturing a plurality of time-sequenced images of a human subject using a digital camera. The digital camera has a digital image sensor, one or more processors in communication with the digital image sensor, and a memory. The digital image sensor, the one or more processors, and the memory are enclosed in a common (i.e., same) housing.

Step 304 of method 300 includes determining, using the one or more processors to execute a machine intelligence module in the memory of the digital camera, a position of a body region of the subject in at least one image of the time-sequenced plurality of images.

Step 306 of method 300 includes identifying, using the one or more processors to execute a biometric analysis on the body region of the plurality of time-sequenced images, an activity state of the subject. In some examples, the activity state of the subject includes a sleep state of the subject. In some examples, executing the biometric analysis includes determining whether the subject is moving by executing an actigraphic analysis of the plurality of time-sequenced images. In some examples, step 306 includes determining a respiration pattern of the subject. In some examples, the respiration pattern includes a respective duration of each inhalation and each exhalation. In some examples, a changing light pattern may be displayed on a remote notification device, the light pattern corresponding to the respiration pattern of the subject.

Step 308 of method 300 includes causing a change in a local environment of the subject based at least in part on the activity state of the subject. For example, causing the change in the local environment of the subject may include causing a change in the temperature of the local environment (e.g., by controlling an HVAC unit or heater). In some examples, causing a change in the local environment of the subject includes causing a change in a light level of the local environment (e.g., by controlling a light source to dim or brighten the lights).

Optional step 310 of method 300 includes communicating information corresponding to the activity state of the subject to a remote notification device (e.g., by the camera using wireless communications). In some examples, step 310 includes detecting a physical characteristic of a local environment of the subject using an environmental sensor; and communicating information corresponding to the physical characteristic to the remote notification device. In some examples, step 310 includes displaying, on the remote notification device, a color corresponding to the current activity state of the subject, the color selected from a plurality of colors each of which corresponds to a different possible activity state. The remote notification device may include a mobile electronic device running a software application configured to display the information on a GUI. The remote notification device may include an ambient information device, such as an electronic device having light, sound, and/or vibration capabilities and configured to produce a pattern or change in response to the information.

Illustrative Data Processing System

Figure 12:
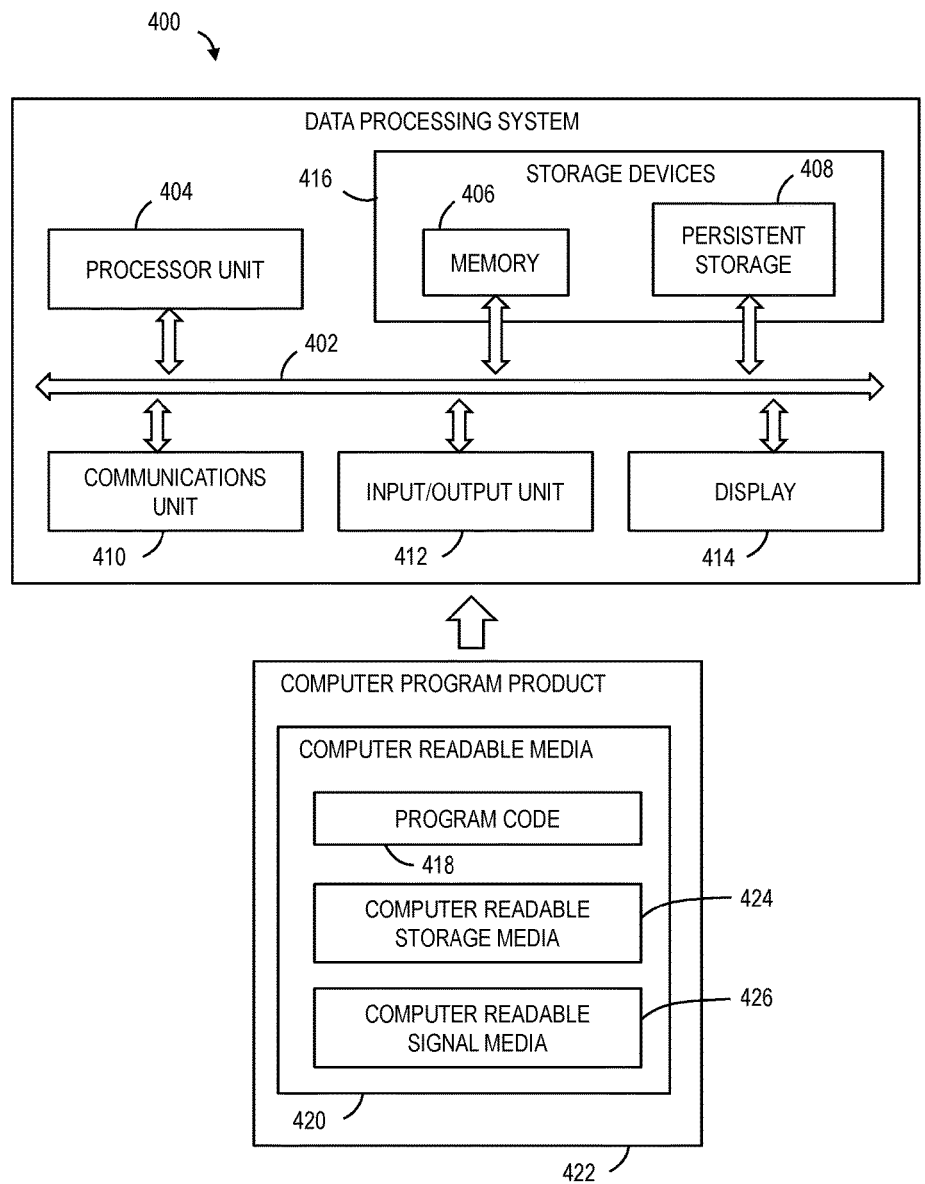
FIG. 12 is a schematic diagram of an illustrative data processing system.

As shown in FIG. 12, this example describes a data processing system 400 (also referred to as a computer) in accordance with aspects of the present disclosure. In this example, data processing system 400 is an illustrative data processing system suitable for implementing aspects of remote biometric monitoring systems. More specifically, systems 10 and 250 may comprise devices that are embodiments of data processing systems (e.g., smartphones, digital cameras, tablets, personal computers) such as camera 12, remote notification devices 18 and 46, camera 200, and the like. Moreover, algorithm 100 and/or algorithms and modules 110, 112, etc., may be executed on or by one or more data processing systems.

In this illustrative example, data processing system 400 includes communications framework 402. Communications framework 402 provides communications between processor unit 404, memory 406, persistent storage 408, communications unit 410, input/output (I/O) unit 412, and display 414. Memory 406, persistent storage 408, communications unit 410, input/output (I/O) unit 412, and display 414 are examples of resources accessible by processor unit 404 via communications framework 402.

Processor unit 404 (e.g., processor 24) serves to run instructions that may be loaded into memory 406. Processor unit 404 may be a number of processors, a multi-processor core, or some other type of processor, depending on the particular implementation. Further, processor unit 404 may be implemented using a number of heterogeneous processor systems in which a main processor is present with secondary processors on a single chip. As another illustrative example, processor unit 404 may be a symmetric multi-processor system containing multiple processors of the same type.

Memory 406 and persistent storage 408 are examples of storage devices 416 (e.g., memory 26). A storage device is any piece of hardware that is capable of storing information, such as, for example, without limitation, data, program code in functional form, and other suitable information either on a temporary basis or a permanent basis.

Storage devices 416 also may be referred to as computer-readable storage devices in these examples. Memory 406, in these examples, may be, for example, a random access memory or any other suitable volatile or non-volatile storage device. Persistent storage 408 may take various forms, depending on the particular implementation.

For example, persistent storage 408 may contain one or more components or devices. For example, persistent storage 408 may be a hard drive, a flash memory, a rewritable optical disk, a rewritable magnetic tape, or some combination of the above. The media used by persistent storage 408 also may be removable. For example, a removable hard drive may be used for persistent storage 408.

Communications unit 410 (e.g., communications module 30), in these examples, provides for communications with other data processing systems or devices. In these examples, communications unit 410 is a network interface card. Communications unit 410 may provide communications through the use of either or both physical and wireless communications links.

Input/output (I/O) unit 412 allows for input and output of data with other devices that may be connected to data processing system 400. For example, input/output (I/O) unit 412 may provide a connection for user input through a keyboard, a mouse, and/or some other suitable input device. Further, input/output (I/O) unit 412 may send output to a printer. Display 414 provides a mechanism to display information to a user.

Instructions (e.g., instructions 32) for the operating system, applications, and/or programs may be located in storage devices 416 (e.g., memory 26), which are in communication with processor unit 404 through communications framework 402. In these illustrative examples, the instructions are in a functional form on persistent storage 408. These instructions may be loaded into memory 406 for execution by processor unit 404. The processes of the different embodiments may be performed by processor unit 404 using computer-implemented instructions, which may be located in a memory, such as memory 406.

These instructions are referred to as program instructions, program code, computer usable program code, or computer-readable program code that may be read and executed by a processor in processor unit 404. The program code in the different embodiments may be embodied on different physical or computer-readable storage media, such as memory 406 or persistent storage 408.

Program code 418 is located in a functional form on computer-readable media 420 that is selectively removable and may be loaded onto or transferred to data processing system 400 for execution by processor unit 404. Program code 418 and computer-readable media 420 form computer program product 422 in these examples. In one example, computer-readable media 420 may be computer-readable storage media 424 or computer-readable signal media 426.

Computer-readable storage media 424 may include, for example, an optical or magnetic disk that is inserted or placed into a drive or other device that is part of persistent storage 408 for transfer onto a storage device, such as a hard drive, that is part of persistent storage 408. Computer-readable storage media 424 also may take the form of a persistent storage, such as a hard drive, a thumb drive, or a flash memory, that is connected to data processing system 400. In some instances, computer-readable storage media 424 may not be removable from data processing system 400.

In these examples, computer-readable storage media 424 is a physical or tangible storage device used to store program code 418 rather than a medium that propagates or transmits program code 418. Computer-readable storage media 424 is also referred to as a computer-readable tangible storage device or a computer-readable physical storage device. In other words, computer-readable storage media 424 is a media that can be touched by a person.

Alternatively, program code 418 may be transferred to data processing system 400 using computer-readable signal media 426. Computer-readable signal media 426 may be, for example, a propagated data signal containing program code 418. For example, computer-readable signal media 426 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some illustrative embodiments, program code 418 may be downloaded over a network to persistent storage 408 from another device or data processing system through computer-readable signal media 426 for use within data processing system 400. For instance, program code stored in a computer-readable storage medium in a server data processing system may be downloaded over a network from the server to data processing system 400. The data processing system providing program code 418 may be a server computer, a client computer, or some other device capable of storing and transmitting program code 418.

The different components illustrated for data processing system 400 are not meant to provide architectural limitations to the manner in which different embodiments may be implemented. The different illustrative embodiments may be implemented in a data processing system including components in addition to and/or in place of those illustrated for data processing system 400. Other components shown in FIG. 12 can be varied from the illustrative examples shown. The different embodiments may be implemented using any hardware device or system capable of running program code. As one example, data processing system 400 may include organic components integrated with inorganic components and/or may be comprised entirely of organic components excluding a human being. For example, a storage device may be comprised of an organic semiconductor.

In another illustrative example, processor unit 404 may take the form of a hardware unit that has circuits that are manufactured or configured for a particular use. This type of hardware may perform operations without needing program code to be loaded into a memory from a storage device to be configured to perform the operations.

For example, when processor unit 404 takes the form of a hardware unit, processor unit 404 may be a circuit system, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, a field programmable logic array, a field programmable gate array, and other suitable hardware devices. With this type of implementation, program code 418 may be omitted, because the processes for the different embodiments are implemented in a hardware unit.

In still another illustrative example, processor unit 404 may be implemented using a combination of processors found in computers and hardware units. Processor unit 404 may have a number of hardware units and a number of processors that are configured to run program code 418. With this depicted example, some of the processes may be implemented in the number of hardware units, while other processes may be implemented in the number of processors.

In another example, a bus system may be used to implement communications framework 402 and may be comprised of one or more buses, such as a system bus or an input/output bus. Of course, the bus system may be implemented using any suitable type of architecture that provides for a transfer of data between different components or devices attached to the bus system.

Additionally, communications unit 410 may include a number of devices that transmit data, receive data, or both transmit and receive data. Communications unit 410 may be, for example, a modem or a network adapter, two network adapters, or some combination thereof. Further, a memory may be, for example, memory 406, or a cache, such as that found in an interface and memory controller hub that may be present in communications framework 402.

The flowcharts and block diagrams described herein illustrate the architecture, functionality, and operation of possible implementations of systems, methods, and computer program products according to various illustrative embodiments. In this regard, each block in the flowcharts or block diagrams may represent a module, segment, or portion of code, which comprises one or more executable instructions for implementing the specified logical function or functions. It should also be noted that, in some alternative implementations, the functions noted in a block may occur out of the order noted in the drawings. For example, the functions of two blocks shown in succession may be executed substantially concurrently, or the functions of the blocks may sometimes be executed in the reverse order, depending upon the functionality involved.

Illustrative Distributed Data Processing System

Figure 13:
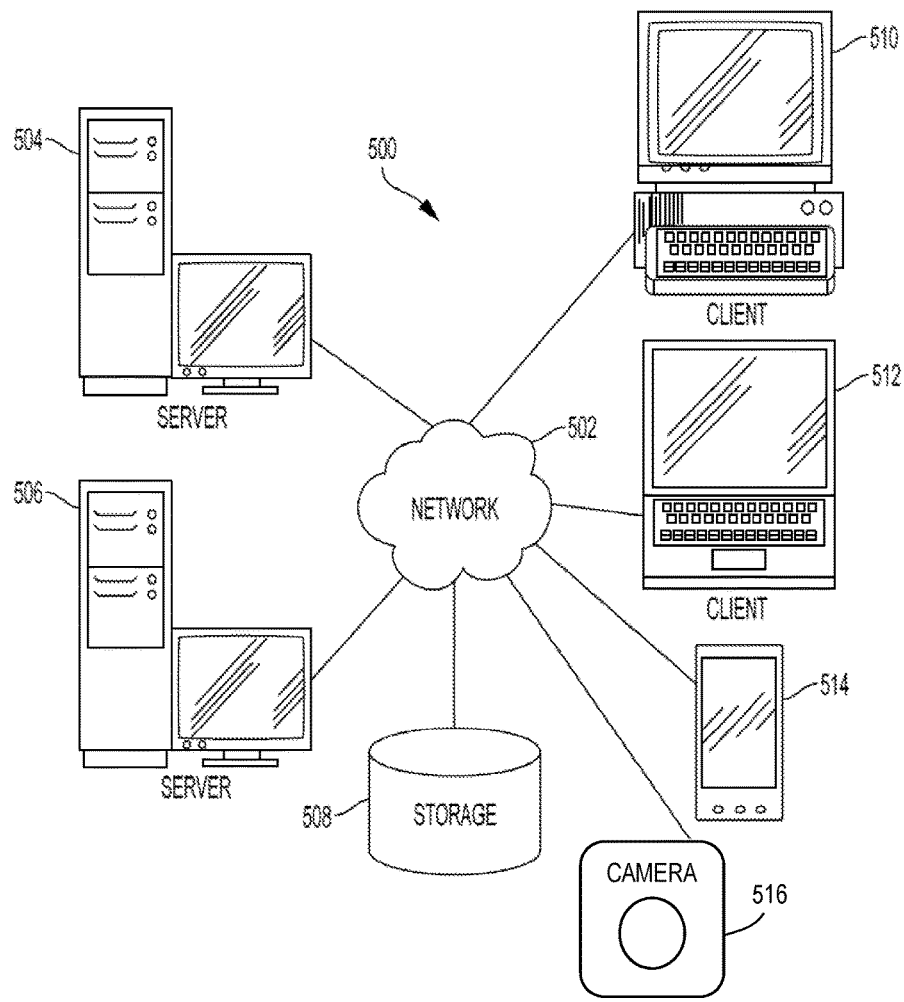
FIG. 13 is a schematic diagram of an illustrative computer network.

As shown in FIG. 13, this example describes a general network data processing system 500, interchangeably termed a network, a computer network, a network system, a distributed data processing system, or a distributed network, aspects of which may be included in one or more illustrative embodiments of remote biometric monitoring systems described herein. For example, one or more algorithms, sub-algorithms, or modules of the digital camera or the remote software application may be executed and/or stored on a network. In some examples, communication between the camera, the remote notification device(s), the environmental sensor(s), and/or the environmental control device(s) may be implemented using a computer network.

It should be appreciated that FIG. 13 is provided as an illustration of one implementation and is not intended to imply any limitation with regard to environments in which different embodiments may be implemented. Many modifications to the depicted environment may be made.

Network data processing system 500 is a network of computers, each of which is an example of data processing system 400, and other components or devices. Network data processing system 500 may include network 502, which is a medium configured to provide communications links between various devices and computers connected together within network data processing system 500. Network 502 may include connections such as wired or wireless communication links, fiber optic cables, and/or any other suitable medium for transmitting and/or communicating data between network devices, or any combination thereof.

In the depicted example, a first network device 504 and a second network device 506 connect to network 502, as does an electronic storage device 508. Network devices 504 and 506 are each examples of data processing system 400, described above. In the depicted example, devices 504 and 506 are shown as server computers. However, network devices may include, without limitation, one or more personal computers, mobile computing devices such as personal digital assistants (PDAs), tablets, and smart phones, handheld gaming devices, wearable devices, tablet computers, routers, switches, voice gates, servers, electronic storage devices, imaging devices, and/or other networked-enabled tools that may perform a mechanical or other function. These network devices may be interconnected through wired, wireless, optical, and other appropriate communication links.

In addition, client electronic devices, such as a client computer 510, a client laptop or tablet 512, and/or a client smartdevice 514, may connect to network 502. Each of these devices is an example of data processing system 400, described above regarding FIG. 12. In some examples, communications-enabled data processing systems on one or more digital cameras 516 may connect to network 502. Client electronic devices 510, 512, 514, and 516 may include, for example, one or more personal computers, network computers, and/or mobile computing devices such as personal digital assistants (PDAs), smart phones, handheld gaming devices, wearable devices, and/or tablet computers, and the like. In the depicted example, server 504 provides information, such as boot files, operating system images, and applications to one or more of client electronic devices 510, 512, and 514. Client electronic devices 510, 512, 514, and 516 may be referred to as "clients" with respect to a server such as server computer 504. Network data processing system 500 may include more or fewer servers and clients or no servers or clients, as well as other devices not shown.

Client smartdevice 514 may include any suitable portable electronic device capable of wireless communications and execution of software, such as a smartphone or a tablet. Generally speaking, the term "smartphone" may describe any suitable portable electronic device having more advanced computing ability and network connectivity than a typical mobile phone. In addition to making phone calls (e.g., over a cellular network), smartphones may be capable of sending and receiving emails, texts, and multimedia messages, accessing the Internet, and/or functioning as a web browser. Smartdevices (e.g., smartphones) may also include features of other known electronic devices, such as a media player, personal digital assistant, digital camera, video camera, and/or global positioning system. Smartdevices (e.g., smartphones) may be capable of connecting with other smartdevices, computers, or electronic devices wirelessly, such as through near field communications (NFC), BLUETOOTH®, WiFi, or mobile broadband networks. Wireless connectively may be established among smartdevices, smartphones, computers, and other devices to form a mobile network where information can be exchanged.

Program code located in system 500 may be stored in or on a computer recordable storage medium, such as persistent storage described, and may be downloaded to a data processing system or other device for use. For example, program code may be stored on a computer recordable storage medium on server computer 504 and downloaded for use to client 510 over network 502 for use on client 510.

Network data processing system 500 may be implemented as one or more of a number of different types of networks. For example, system 500 may include an intranet, a local area network (LAN), a wide area network (WAN), or a personal area network (PAN). In some examples, network data processing system 500 includes the Internet, with network 502 representing a worldwide collection of networks and gateways that use the transmission control protocol/Internet protocol (TCP/IP) suite of protocols to communicate with one another. At the heart of the Internet is a backbone of high-speed data communication lines between major nodes or host computers. Thousands of commercial, governmental, educational and other computer systems may be utilized to route data and messages. In some examples, network 500 may be referred to as a "cloud." In those examples, each server 504 may be referred to as a cloud computing node, and client electronic devices may be referred to as cloud consumers, or the like. FIG. 13 is intended as an example, and not as an architectural limitation for any illustrative embodiments.

Additional Examples

This section describes additional aspects and features of remote biometric monitoring systems and related methods, presented without limitation as a series of paragraphs, some or all of which may be alphanumerically designated for clarity and efficiency. Each of these paragraphs can be combined with one or more other paragraphs, and/or with disclosure from elsewhere in this application, including the materials incorporated by reference in the Cross-References, in any suitable manner. Some of the paragraphs below expressly refer to and further limit other paragraphs, providing without limitation examples of some of the suitable combinations.

A. A system for monitoring the health of a sleeping child, comprising:
  a camera configured to capture images of a sleeping child;
  at least one environmental sensor chosen from the set consisting of a humidity sensor and a temperature sensor, the sensor configured to capture data from a local environment in which the child is sleeping;
  a microphone configured to capture sounds from the local environment in which the child is sleeping;
  a processor configured to receive and analyze the images and data to determine (i) a plurality of biometric parameters relating to the child including at least length of sleep, sleep quality, sleep cycle information, and a breathing pattern, and (ii) whether the local environment falls within predetermined temperature or humidity limits; and
  a remote notification device configured to provide information relating to the biometric parameters and the local environment to a user located out of sight of the child.

A1. The system of paragraph A, wherein the remote notification device includes a video screen.

A2. The system of paragraph A1, wherein the video screen is a smart phone screen.

A3. The system of paragraph A1, wherein the video screen is a tablet screen.

A4. The system of paragraph A1, wherein the video screen is a personal computer screen.

A5. The system of paragraph A1, wherein the video screen is included in a dedicated video monitoring device.

A6. The system of paragraph A, wherein the remote notification device is a portable device configured to receive commands wirelessly from the processor and to provide information to the user in the form of light, sound and vibration.

A7. The system of paragraph A, wherein the at least one environmental sensor includes both a temperature sensor and a humidity sensor.

A8. The system of paragraph A7, wherein the temperature sensor is wearable by the child.

A9. The system of paragraph A, wherein the processor is further configured to analyze the images and data to determine a heart rate of the child.

A10. The system of paragraph A, wherein the remote notification device is configured to generate an alarm signal corresponding to one of a plurality of predetermined alarm triggers.

A11. The system of paragraph A10, wherein the alarm triggers include at least one alarm trigger selected from the set consisting of a breathing problem, a failure to obtain a breathing signal, an unacceptable physical disposition of the child, a seizure, an unacceptable change in room temperature or humidity, excessive or abnormal coughing, and crying.

A12. The system of paragraph A, wherein the processor is further configured to analyze the images and data to determine a breathing rate of the child.

B. A system for monitoring the health and local environment of a sedentary person, comprising:
a camera configured to capture images of a sedentary person;
at least one environmental sensor chosen from the set consisting of a humidity sensor and a temperature sensor, the sensor configured to capture data from a local environment of the person;
a processor configured to receive and analyze the images and data to determine a breathing pattern of the person and also to determine whether the local environment of the person falls within predetermined temperature or humidity limits; and
a remote notification device configured to provide information relating to the biometric parameters and the local environment to a user located out of sight of the person.

B1. The system of paragraph B, further comprising a microphone configured to capture sounds made by the person, and wherein the processor is further configured to identify coughing sounds and to determine a coughing frequency of the person.

B2. The system of paragraph B, wherein the at least one environmental sensor includes a temperature sensor configured to be worn by the person.

B3. The system of paragraph B, wherein the remote notification device is configured to receive commands wirelessly from the processor and to provide information to the user in the form of light, sound and vibration.

B4. The system of paragraph B3, wherein the remote notification device is configured to display a different color corresponding to each of a plurality of sleep states of the person.

B5. The system of paragraph B3, wherein the remote notification device is configured to display a changing light pattern corresponding to a breathing pattern of the person.

B6. The system of paragraph B3, wherein the remote notification device is configured to alert the user if the person exhibits any of a plurality of predetermined alarm conditions.

B7. The system of paragraph B6, wherein the alarm conditions include a breathing problem.

B8. The system of paragraph B6, wherein the alarm conditions include an unacceptable location of the person.

B9. The system of paragraph B6, wherein the alarm conditions include excessive coughing of the person.

B10. The system of paragraph B6, wherein the alarm conditions include an unacceptable temperature of the local environment of the person.

B11. The system of paragraph B6, wherein the alarm conditions include an unacceptable body temperature of the person.

B12. The system of paragraph B, wherein the at least one environmental sensor includes an air quality sensor configured to measure air quality of the local environment of the person.

B13. The system of paragraph B, wherein the remote notification device is a mobile electronic device running a software application configured to receive information from the processor and to display the information on a display screen.

C. A system for monitoring the health and local environment of a person, comprising:
a camera configured to capture images of a person;
at least one environmental sensor chosen from the set consisting of a humidity sensor and a temperature sensor, the sensor configured to capture data from a local environment of the person;
a processor configured to receive and analyze the images and data to determine a breathing pattern of the person and whether the local environment of the person falls within predetermined temperature or humidity limits; and
a computer software application running on a portable electronic device and configured to receive information from the processor and to display the information on a display screen of the portable electronic device.

C1. The system of paragraph C, further comprising a remote notification device configured to receive information wirelessly from the processor and to provide information relating to the biometric parameters and the local environment to a user located out of sight of the person using lights, sounds and/or vibrations.

C2. The system of paragraph C1, wherein the remote notification device is configured to display a different colored light corresponding to each of a plurality of biometric conditions of the person.

C3. The system of paragraph C1, wherein the remote notification device is configured to display a dynamic light pattern corresponding to a breathing pattern of the person.

C4. The system of paragraph C1, wherein the remote notification device is configured to emit an audible alarm sound corresponding to an unacceptable condition of the person.

C5. The system of paragraph C4, wherein the unacceptable condition includes at least one indication of an ear infection.

C6. The system of paragraph C5, wherein the at least on indication includes excessive contact between a hand of the person and an ear of the person.

C7. The system of paragraph C, wherein the portable electronic device is configured to display the images of the person and also to display at least one biometric condition of the person.

D0. A system for remotely monitoring a sleeping subject, the system comprising:
a digital camera configured to capture images of a subject, the camera including a digital image sensor, one or more processors in communication with the digital image sensor, and a memory, wherein the digital image sensor, the one or more processors, and the memory are enclosed in a same housing;

an environmental sensor in communication with the one or more processors of the digital camera, the environmental sensor configured to detect a physical characteristic of a local environment of the subject;

an environmental control device in communication with the one or more processors of the digital camera, the environmental control device configured to produce a change in the local environment of the subject; and a set of instructions stored in the memory of the digital camera and executable locally by the one or more processors to:

receive a sensed input from the environmental sensor and a plurality of time-sequenced images of the subject from the digital image sensor;

determine, using an artificial intelligence module, a position of a body region of the subject in a subset of images of the time-sequenced plurality of images;

identify, using the position of the body region determined by the artificial intelligence module to perform a biometric analysis on the plurality of time-sequenced images, an activity state of the subject; and cause a change in the environmental control device based on the sensed input and the activity state of the subject.

D1. The system of D0, wherein the plurality of time-sequenced images are uncompressed.

D2. The system of any of paragraphs D0 through D1, wherein the body region of the subject includes a torso region.

D3. The system of any of paragraphs D0 through D2, wherein the biometric analysis includes determining whether the subject is moving by performing an actigraphic analysis of the plurality of time-sequenced images of the subject.

D4. The system of any of paragraphs D0 through D3, wherein identifying the activity state of the subject includes identifying a sleep state of the subject.

D5. The system of any of paragraphs D0 through D4, wherein the subset of images consists of a single image.

D6. The system of any of paragraphs D0 through D5, wherein the biometric analysis further includes determining a respiration pattern of the subject.

D7. The system of D6, the respiration pattern comprising a respective duration of each inhalation and each exhalation.

D8. The system of D6 or D7, wherein causing the change in the environmental control device is further based on the respiration pattern of the subject.

D9. The system of any of paragraphs D0 through D8, further comprising a tripod support having the digital camera articulatably attached thereto.

D10. The system of D9, wherein the tripod includes a pair of short legs each having a first permanent length, and a long leg having a second permanent length at least fifty percent longer than the first permanent length.

D11. The system of D10, wherein the second length is approximately twice as long as the first permanent length.

D12. The system of D10 or D11, wherein the long leg of the tripod includes a hook interface, such that the digital camera is configured to be hung by the hook interface on a hook protruding from a substantially vertical support surface with the pair of short legs providing a stabilizing standoff against the support surface.

D13. The system of any of paragraphs D0 through D12, wherein the artificial intelligence module comprises a neural network.

D14. The system of D13, wherein the neural network is a convolutional neural network.

D15. The system of D14, wherein the convolutional neural network is fully convolutional.

D16. The system of any of paragraphs D0 through D15, further comprising a remote notification device in communication with the digital camera, the remote notification device configured to provide information relating to the activity state of the subject to a user located out of sight of the subject.

D17. The system of D16, wherein the remote notification device comprises a portable electronic device running a software application configured to display information relating to the activity state of the subject on a graphical user interface.

D18. The system of D16 or D17, wherein the remote notification device comprises an ambient information device configured to change a light display of the device in response to the activity state of the subject.

D19. The system of any of paragraphs D0 through D18, wherein the environmental sensor comprises a microphone.

D20. The system of D19, wherein the sensed input is sound information from the microphone, and the biometric analysis further comprises determining whether the subject is producing a selected noise based on the sensed input.

D21. The system of D20, wherein the selected noise is a cough.

D22. The system of any of paragraphs D0 through D21, wherein the environmental sensor is chosen from the set consisting of a temperature sensor, a humidity sensor, and an air quality sensor.

D23. The system of any of paragraphs D0 through D22, wherein the environmental control device is chosen from the set consisting of a lamp, an audio speaker, an HVAC device, and a humidity control device.

E0. A system for remotely monitoring a sleeping person, the system comprising:

a digital camera configured to capture images of a person, the camera including a digital image sensor, one or more processors in communication with the digital image sensor, and a memory, wherein the digital image sensor, the one or more processors, and the memory are enclosed in a same housing;

a remote notification device in communication with a user located out of sight of the person; and a set of instructions stored in the memory of the digital camera and executable locally by the one or more processors to:

receive a plurality of time-sequenced images of the person from the digital image sensor;

determine, using an artificial intelligence module, a position of a body region of the person in at least one image of the time-sequenced plurality of images;

identify, using the position of the body region determined by the artificial intelligence to perform a biometric analysis on the plurality of time-sequenced images, an activity state of the person; and communicate information corresponding to the activity state of the person to the user via the remote notification device.

E1. The system of E0, wherein the plurality of time-sequenced images are uncompressed.

E2. The system of any of paragraphs E0 through E1, wherein the biometric analysis includes determining a movement state of the person by performing an actigraphic analysis of the plurality of time-sequenced images.

E3. The system of any of paragraphs E0 through E2, wherein the digital camera is a video camera.

E4. The system of any of paragraphs E0 through E3, wherein the activity state of the person includes a sleep state.

E5. The system of E4, wherein the remote notification device is configured to display a color corresponding to the current sleep state of the person, the color selected from a plurality of colors each of which corresponds to a different possible sleep state.

E6. The system of any of paragraphs E0 through E5, wherein the set of instructions are further executable locally by the one or more processors to determine a respiration pattern of the person.

E7. The system of E6, the respiration pattern comprising a respective duration of each inhalation and each exhalation.

E8. The system of E6 or E7, wherein the remote notification device is configured to display a changing light pattern corresponding to the respiration pattern of the person.

E9. The system of any of paragraphs E0 through E8, wherein the remote notification device is in wireless communication with the digital camera over a local area network.

E10. The system of any of paragraphs E0 through E9, wherein the remote notification device is in direct communication with the digital camera using a wireless protocol.

E11. The system of any of paragraphs E0 through E10, wherein the remote notification device comprises a portable electronic device running a software application configured to display information relating to the activity state of the subject on a graphical user interface.

E12. The system of any of paragraphs E0 through E11, wherein the artificial intelligence module comprises a neural network.

F0. A method for remotely monitoring a sleep state of a human subject, the method comprising:
capturing a plurality of time-sequenced images of a human subject using a digital camera having a digital image sensor, one or more processors in communication with the digital image sensor, and a memory, wherein the digital image sensor, the one or more processors, and the memory are enclosed in a same housing;
determining, using the one or more processors to execute a machine intelligence module in the memory of the digital camera, a position of a body region of the subject in at least one image of the time-sequenced plurality of images;
identifying, using the one or more processors to execute a biometric analysis on the body region of the plurality of time-sequenced images, an activity state of the subject; and
causing a change in a local environment of the subject based at least in part on the activity state of the subject.

F1. The method of F0, wherein the activity state of the subject includes a sleep state of the subject.

F2. The method of any of paragraphs F0 through F1, wherein executing the biometric analysis includes determining whether the subject is moving by executing an actigraphic analysis of the plurality of time-sequenced images.

F3. The method of any of paragraphs F0 through F2, wherein causing the change in the local environment of the subject includes causing a change in the temperature of the local environment.

F4. The method of any of paragraphs F0 through F3, wherein causing a change in the local environment of the subject includes causing a change in a light level of the local environment.

F5. The method of any of paragraphs F0 through F4, further comprising communicating information corresponding to the activity state of the subject to a remote notification device.

F6. The method of F5, further comprising
detecting a physical characteristic of a local environment of the subject using an environmental sensor; and
communicating information corresponding to the physical characteristic to the remote notification device.

F7. The method of F5 or F6, further comprising:
displaying, on the remote notification device, a color corresponding to the current activity state of the subject, the color selected from a plurality of colors each of which corresponds to a different possible activity state.

F8. The method of any of paragraphs F0 through F7, further including determining a respiration pattern of the subject.

F9. The method of F8, the respiration pattern comprising a respective duration of each inhalation and each exhalation.

F10. The method of F8 or F9, further comprising:
displaying a changing light pattern on a remote notification device, the light pattern corresponding to the respiration pattern of the subject.

Advantages, Features, Benefits

The different embodiments and examples of the remote biometric monitoring systems and methods described herein provide several advantages over known solutions. For example, illustrative embodiments and examples described herein allow noninvasive and non-contact monitoring of a sleeping subject.

Additionally, and among other benefits, illustrative embodiments and examples described herein allow enhanced privacy and reliability by performing image processing and analysis locally, on-camera. The user does not need to rely on an Internet connection or a remote server, unless desired.

Additionally, and among other benefits, illustrative embodiments and examples described herein include multiple biometric analyses, all of which may be combined and correlated to more accurately and/or more granularly determine the activity state of the subject.

Additionally, and among other benefits, illustrative embodiments and examples described herein provide automatic and intelligent control of the local environment in response to detected activity states and/or conditions.

Additionally, and among other benefits, illustrative embodiments and examples described herein provide on-camera actigraphic analysis of raw, uncompressed images, reducing error rates and improving accuracy.

No known system or device can perform these functions, particularly with respect to sleep monitoring. Thus, the illustrative embodiments and examples described herein are particularly useful for monitoring the sleep of infants and children. However, not all embodiments and examples described herein provide the same advantages or the same degree of advantage.

CONCLUSION

The disclosure set forth above may encompass multiple distinct examples with independent utility. Although each of these has been disclosed in its preferred form(s), the specific embodiments thereof as disclosed and illustrated herein are not to be considered in a limiting sense, because numerous variations are possible. To the extent that section headings are used within this disclosure, such headings are for organizational purposes only. The subject matter of the invention(s) includes all novel and nonobvious combinations and subcombinations of the various elements, features, functions, and/or properties disclosed herein. The following claims particularly point out certain combinations and subcombinations regarded as novel and nonobvious. Other combinations and subcombinations of features, functions, elements, and/or properties may be claimed in applications claiming priority from this or a related application. Such claims, whether broader, narrower, equal, or different in scope to the original claims, also are regarded as included within the subject matter of the present disclosure.

What is claimed is:

1. A system for remotely monitoring a sleeping subject, the system comprising:
    a digital camera configured to capture images of a subject, the digital camera including a digital image sensor, one or more local processors in communication with the digital image sensor, and a memory, wherein the digital image sensor, the one or more local processors, and the memory are enclosed in a same housing, and wherein no sensors or markers are attached to the subject;
    a tripod support having the digital camera articulatably attached thereto, wherein the tripod support includes a pair of short legs each having a first permanent length, and a long leg having a second permanent length at least fifty percent longer than the first permanent length;
    an environmental sensor in communication with the one or more local processors of the digital camera, the environmental sensor configured to detect a physical characteristic of a local environment of the subject;
    an environmental control device in communication with the one or more local processors of the digital camera, the environmental control device configured to produce a change in the local environment of the subject; and
    a set of instructions stored in the memory of the digital camera and executable locally by the one or more local processors to:
        receive a sensed input from the environmental sensor and a plurality of time-sequenced images of the subject from the digital image sensor;
        determine a position of a torso region of the subject using an artificial intelligence module trained to determine a presence and a position of the subject in a subset of images of the time-sequenced plurality of images;
        identify, using the position of the torso region determined by the artificial intelligence module to perform a biometric analysis on an uncompressed version of the plurality of time-sequenced images, an activity state of the subject; and
        cause a change in the environmental control device based on the sensed input and the activity state of the subject.

2. The system of claim 1, wherein the biometric analysis includes determining whether the subject is moving by performing an actigraphic analysis of the plurality of uncompressed, time-sequenced images of the subject.

3. The system of claim 1, wherein identifying the activity state of the subject includes identifying a sleep state of the subject.

4. The system of claim 1, wherein the subset of images consists of a single image.

5. The system of claim 1, wherein the biometric analysis further includes determining a respiration pattern of the subject.

6. The system of claim 5, wherein causing the change in the environmental control device is further based on the respiration pattern of the subject.

7. The system of claim 1, wherein the artificial intelligence module comprises a neural network.

8. The system of claim 1, further comprising a remote notification device in communication with the digital camera, the remote notification device configured to provide information relating to the activity state of the subject to a user located out of sight of the subject.

9. A system for remotely monitoring a sleeping person, the system comprising:
    a digital camera configured to capture images of a person, the digital camera including a digital image sensor, one or more local processors in communication with the digital image sensor, and a memory, wherein the digital image sensor, the one or more local processors, and the memory are enclosed in a same housing, and wherein no sensors or markers are attached to the person;
    a tripod support having the digital camera articulatably attached thereto, wherein the tripod support includes a pair of short legs each having a first permanent length, and a long leg having a second permanent length at least fifty percent longer than the first permanent length;
    a remote notification device in communication with a user located out of sight of the person; and
    a set of instructions stored in the memory of the digital camera and executable locally by the one or more local processors to:
        receive a plurality of time-sequenced images of the person from the digital image sensor;
        determine a position of a torso region of the person, using an artificial intelligence module trained to determine a presence and a position of the person in at least one image of the time-sequenced plurality of images;
        identify, using the position of the torso region determined by the artificial intelligence module to perform a biometric analysis on an uncompressed version of the plurality of time-sequenced images, an activity state of the person; and
        communicate information corresponding to the activity state of the person to the user via the remote notification device.

10. The system of claim 9, wherein the biometric analysis includes determining a movement state of the person by performing an actigraphic analysis of the plurality of uncompressed, time-sequenced images.

11. The system of claim 9, wherein the activity state of the person includes a sleep state.

12. The system of claim 9, wherein the set of instructions are further executable locally by the one or more local processors to determine a respiration pattern of the person.

13. A method for remotely monitoring a sleep state of a human subject, the method comprising:
    capturing a plurality of time-sequenced images of a human subject using a digital camera having a digital image sensor, one or more local processors in communication with the digital image sensor, and a memory, wherein the digital image sensor, the one or more local processors, and the memory are enclosed in a same housing, wherein no sensors or markers are attached to the human subject, and wherein the digital camera is articulably attached to a tripod support including a pair of short legs each having a first permanent length and a long leg having a second permanent length at least fifty percent longer than the first permanent length;
    determining, using the one or more local processors to execute a machine intelligence module in the memory of the digital camera, a position of a torso region of the human subject, wherein the machine intelligence module is trained to determine a presence and a position of the human subject in at least one image of the time-sequenced plurality of images;

identifying, using the one or more local processors to execute a biometric analysis on an area associated with the torso region in an uncompressed version of the time-sequenced plurality of images, an activity state of the human subject; and causing a change in a local environment of the human subject based at least in part on the activity state of the human subject.

14. The method of claim 13, wherein the activity state of the human subject includes a sleep state of the human subject.

15. The method of claim 13, wherein executing the biometric analysis includes determining whether the human subject is moving by executing an actigraphic analysis of the time-sequenced plurality of images.

16. The method of claim 13, further including determining a respiration pattern of the human subject.

17. The method of claim 16, the respiration pattern comprising a respective duration of each inhalation and each exhalation.

18. The method of claim 16, further comprising:

displaying a changing light pattern on a remote notification device, the changing light pattern corresponding to the respiration pattern of the human subject.

19. The method of claim 13, wherein determining the position of the torso region of the human subject in the at least one image of the time-sequenced plurality of images includes determining coordinates of the torso region and providing a bounding box generally identifying where the human subject is located.

20. The method of claim 19, wherein identifying the activity state of the human subject includes using the one or more local processors to execute the biometric analysis on a respective area of each of the plurality of uncompressed, time-sequenced images, wherein the respective area corresponds to the bounding box.

21. The method of claim 13, wherein determining the position of the torso region of the human subject in the at least one image of the time-sequenced plurality of images includes determining a confidence level with respect to the presence of the human subject in the at least one image.

* * * * *